(12) United States Patent
Nath et al.

(10) Patent No.: US 10,982,181 B2
(45) Date of Patent: Apr. 20, 2021

(54) DEVICES FOR CELL CULTURE AND METHODS OF MAKING AND USING THE SAME

(71) Applicant: Los Alamos National Security, LLC, Los Alamos, NM (US)

(72) Inventors: Pulak Nath, Los Alamos, NM (US); Jen-Huang Huang, Los Alamos, NM (US)

(73) Assignee: Triad National Security, LLC, Los Alamos, NM (US)

( * ) Notice: Subject to any disclaimer, the term of this patent is extended or adjusted under 35 U.S.C. 154(b) by 0 days.

(21) Appl. No.: 15/697,306

(22) Filed: Sep. 6, 2017

(65) Prior Publication Data

US 2018/0066220 A1 Mar. 8, 2018

Related U.S. Application Data

(60) Provisional application No. 62/384,451, filed on Sep. 7, 2016.

(51) Int. Cl.
*B01L 3/00* (2006.01)
*C12M 3/00* (2006.01)
(Continued)

(52) U.S. Cl.
CPC ............ *C12M 23/16* (2013.01); *C12M 21/08* (2013.01); *C12M 23/26* (2013.01); *C12M 25/10* (2013.01); *C12M 25/14* (2013.01); *C12M 29/10* (2013.01); *C12M 33/12* (2013.01); *C12M 35/04* (2013.01); *C12M 35/08* (2013.01); *C12M 41/40* (2013.01); *C12N 5/0697* (2013.01); *G01N 33/5032* (2013.01); *C12N 2502/095* (2013.01); *C12N 2502/1305* (2013.01); *C12N 2502/1323* (2013.01); *C12N 2502/27* (2013.01); *C12N 2502/28* (2013.01); *C12N 2502/30* (2013.01);
(Continued)

(58) Field of Classification Search
CPC ...... C12M 25/12; C12M 25/10; C12M 25/04; C12M 29/16
See application file for complete search history.

(56) References Cited

U.S. PATENT DOCUMENTS

2004/0132175 A1* 7/2004 Vetillard ................ C12M 25/16
435/297.1
2004/0203147 A1* 10/2004 Triffitt .................... C12M 21/08
435/400
(Continued)

FOREIGN PATENT DOCUMENTS

WO WO 2016/049363 3/2016
WO WO 2016/049365 3/2016

OTHER PUBLICATIONS

Huang et al., "Hollow fiber integrated microfluidic platforms for in vitro co-culture of multiple cell types," *Biomed. Microdevices* 18:88, 2016.
(Continued)

*Primary Examiner* — Nathan A Bowers
(74) *Attorney, Agent, or Firm* — Klarquist Sparkman, LLP

(57) ABSTRACT

Devices and systems for cell culture that include one or more hollow fibers or channels integrated into a chamber are provided. The hollow fibers or channels and/or the chamber are seeded with one or more cell types. Methods of co-culturing two or more cell types in the devices are also provided.

16 Claims, 15 Drawing Sheets

(51) Int. Cl.
    *C12M 3/06*     (2006.01)
    *C12M 1/12*     (2006.01)
    *C12N 5/071*     (2010.01)
    *G01N 33/50*     (2006.01)
    *C12M 1/42*     (2006.01)
    *C12M 1/34*     (2006.01)
    *C12M 1/00*     (2006.01)
    *C12M 1/26*     (2006.01)

(52) U.S. Cl.
    CPC ...... *C12N 2521/00* (2013.01); *C12N 2533/78* (2013.01)

(56) References Cited

U.S. PATENT DOCUMENTS

2007/0105222 A1*   5/2007   Wolfinbarger ......... C12M 21/08
                                                                                                                                          435/373

2009/0191631 A1*   7/2009   Bornennann ......... C12M 23/10
                                                                                                                                          435/395
2013/0295598 A1*   11/2013   Marx ..................... C12M 21/08
                                                                                                                                         435/29
2014/0142370 A1*   5/2014   Wong ..................... C12M 25/14
                                                                                                                                        600/36

OTHER PUBLICATIONS

Krause et al., "A Novel 3D In Vitro Culture Model to Study Stromal-Epithelial Interactions in the Mammary Gland," *Tissue Engineering*, vol. 14, No. 3, pp. 261-271, 2008.

Villasante et al., "Recapitulating the Size and Cargo of Tumor Exosomes in a Tissue-Engineered Model," *Theranostics*, vol. 6, No. 8, pp. 1119-1130, 2016.

* cited by examiner

DEVICES FOR CELL CULTURE AND METHODS OF MAKING AND USING THE SAME

CROSS REFERENCE TO RELATED APPLICATION

This claims the benefit of U.S. Provisional Application No. 62/384,451, filed Sep. 7, 2016, which is incorporated herein by reference in its entirety.

ACKNOWLEDGMENT OF GOVERNMENT SUPPORT

This invention was made with government support under Contract No. DE-AC52-06NA25396 awarded by the U.S. Department of Energy. The government has certain rights in the invention.

FIELD

This disclosure relates to devices for cell culture, particularly microfluidic devices and methods of making and using the devices.

BACKGROUND

In vitro models play ubiquitous roles in contemporary medicine. These models have helped identify multiple factors within the breast cancer micro-environment that are directly related to the disease condition. Among these factors, the interaction between cancer cells and all of the surrounding stromal cells, the effect of the stiffness of the extra cellular matrix (ECM), and the effect of oxygen/nutrient gradients have been the subject of many in vitro experiments. These studies indicate that cancer is a heterogeneous disease. Therefore, although informative, the ability to study only one interaction in the absence of the others is not sufficient to obtain complete understanding of the true scenario. Therefore, new in vitro models that are capable of more closely recapitulating the tissue micro-environments are needed to perform complete mechanistic studies on normal tissue and cancer.

SUMMARY

Disclosed herein are integrated microfluidic devices and systems that can be used to co-culture two or more cell types. The disclosed devices and systems permit culture of each cell type in an individual cell culture medium (such as a medium specific for the particular cell type), while providing fluid communication between the one or more cell types. In addition, in some examples, the disclosed devices and systems can be used to dynamically modulate the stiffness of the environment of the cells, for example, by applying pressure to a hydrogel matrix surrounding the cells.

In some embodiments, the disclosed devices include a chamber including one or more channels (for example, 1, 2, 3, 4, 5, 6, 7, 8, 9, 10, 12, 15, 20, or more channels) extending through the chamber, wherein the chamber includes an upper wall, a lower wall, and at least two side walls. The one or more channels have a central lumen, an elongated body having an inner surface and an outer surface and two openings, and can have a circular cross-section (e.g., hollow fibers) or a rectangular cross-section (or other shape) and have at least one surface or portion thereof that is porous or permeable to fluid (for example, including one or more pores). The chamber also includes at least one inlet and outlet for inserting and removing fluid, and may include at least one vent channel (such as one inlet and/or outlet) in one of the side walls. The device also includes at least one opening in each of two opposite side walls to accommodate the at least one channel extending through the chamber, or tubing connected to the channel. The chamber also includes at least one wall (e.g., a top, bottom, and/or side wall) that includes at least a portion that is a flexible substrate or membrane. In some examples, the device also includes a fluid or a hydrogel matrix located in the chamber, for example, surrounding the one or more channels.

In some embodiments, the device also includes a second chamber located above and in contact with the upper wall of the first chamber and/or a third chamber located below and in contact with the lower wall of the first chamber, wherein at least one of the upper wall of the first chamber and the lower wall of the first chamber, or a portion thereof, is a flexible substrate or membrane. In some examples, at least one cell type is seeded in the channel. The device may also include two or more different cells types, for example, seeded in individual channels and/or the chamber.

In some embodiments, the channels have a horizontal orientation in the chamber. In other embodiments, the channels have a vertical orientation in the chamber. In some examples, the channels are present in the chamber in a parallel or planar arrangement, while in other examples, the channels are in a non-planar arrangement. In one example, the channels are arranged in the chamber in one or more substantially concentric rings.

Other embodiments include a system including a device of the disclosure and one or more cell types. In one embodiment, a system includes a chamber including two or more channels (for example, 2, 3, 4, 5, 6, 7, 8, 9, 10, 12, 15, 20, or more channels) extending through the channel, wherein the chamber includes an upper wall, a lower wall, and at least four side walls. The one or more channels have a central lumen, an elongated body having an inner surface and an outer surface and two openings and can be hollow fibers or channels with a rectangular (or other shape) cross-section and have at least one surface or portion thereof that is porous or permeable to fluid (for example, including one or more pores). The chamber also includes at least one inlet and outlet for inserting and removing fluid, and may include at least one vent channel (such as one inlet and/or outlet) in one of the side walls and at least one opening in each of two opposite side walls to accommodate the channel or tubing connected to the channel. The device also includes at least one wall (top, bottom, and/or side wall) that includes at least a portion that is a flexible substrate. At least one of the channels includes cells which are attached to or associated with the inner surface of the channel and at least one of the channels does not include cells. In some embodiments, the system further includes at least one cell type in the chamber, which may be the same or different than the cells in the at least one channel. The system optionally also includes a fluid or matrix (such as a hydrogel matrix) in the chamber, for example, surrounding the channels extending through the chamber.

Also disclosed are methods of culturing cells (such as two or more different cell types) in the disclosed devices. In some embodiments, the methods include seeding one or more of the channels with cells, contacting the cells with a culture medium (for example, by flowing a cell culture medium through the channel containing the cells), and incubating the cells under conditions sufficient for growth, survival, and/or differentiation. In some examples, the methods also include seeding the chamber with at least one cell type. The cell types in the at least one channel and the chamber may be the same or different. In addition, in examples, where two or more channels are seeded with the cells, the cell type in each of the channels may be the same or different from one another, and the medium flowed through each channel may be the same or different. In additional examples, the methods include flowing medium through at least one channel in the device that does not include cells (for example, a medium for support of cells in the chamber). In some examples, the methods further include measuring one or more characteristics of the cells, including but not limited to analyzing exosomes secreted by one or more of the cells.

In some embodiments, the chamber includes a hydrogel matrix surrounding the channels and the method includes modulating (for example, increasing or decreasing) the pressure applied to the flexible substrate on at least one side of the first chamber. The change in pressure applied to the flexible substrate modulates (for example, increases or decreases) the stiffness of the hydrogel surrounding the one or more channels.

The foregoing and other features of the disclosure will become more apparent from the following detailed description, which proceeds with reference to the accompanying figures.

BRIEF DESCRIPTION OF THE DRAWINGS

FIG. 1A is a schematic of a single HF integrated microfluidic device where independent liquid streams can flow into the HF or the chamber. FIG. 1B is a schematic of a multiple HF integrated device, where each HF has an independent liquid stream. FIG. 1C is a schematic of a multiple HF integrated device where the all the HFs are permitted the same liquid stream.

FIG. 4A is a schematic showing regions of leakage between top and middle layers of the device (arrows) and FIG. 4B is a schematic drawing illustrating how liquid can leak from a gap between the layers (arrow). FIG. 4C is a schematic diagram showing a device with integrated silicon membrane, which prevents leakage, and the location of the membrane is schematically shown in FIG. 4D.

FIG. 5A is a schematic showing the cell seeding method using a pressurized flow. FIG. 5B is an SEM image showing the coverage of cells on the lumen of HF after seeding. Scale bar=50 µm. FIG. 5C is a graph showing a comparison of seeding techniques with (pressurized) and without (static) pressurized injection. FIG. 5D is a microscope image (100×) showing live/dead staining of A549 cells after seeding in the lumen of HF. FIG. 5E is a graph showing the effect of surface coverage of seeded cells corresponding to different lengths of attachment times after seeding.

FIG. 6A is a schematic diagram showing culture of BEAS-2B cells inside the lumen of the HF (luminal) and culture of HLMVE cells in the chamber (apical). FIGS. 6B and 6C are microscope images acquired at 100× magnification of the luminal cells (FIG. 6B) and apical cells (FIG. 6C). Scale bar=100 µm.

FIG. 7A is a schematic diagram showing culture of BEAS-2B cells in the lumen of HFs 1, 3, and 5 and culture of HLMVE cells in the lumen of HFs 2 and 4. FIG. 7B is a series of microscope images acquired at 100× magnification from the lumen of each HF. Scale bar=100 µm.

DETAILED DESCRIPTION

Figure 1C:
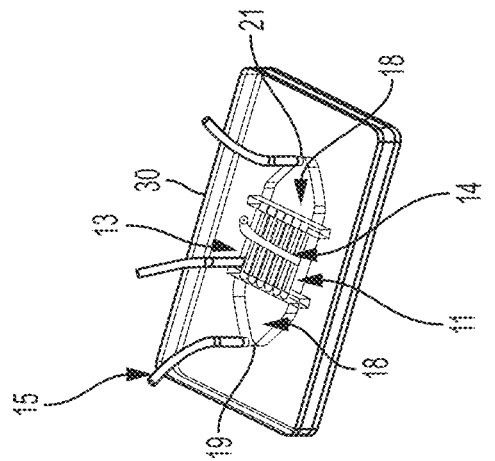
FIGS. 1A-1C are a series of schematic drawings of HF integrated microfluidic devices.

Developing tubular structures in situ using common fabrication techniques available for microfluidics (Sia et al.,

*Electrophoresis* 24:3563-3576, 2003) is not straightforward. However, prefabricated HFs can be obtained and manually installed into microfluidic chambers. Integrating prefabricated HFs into microfluidic platforms presents a challenge of placing tubular structures into planar systems. For fabrication, a rapid prototyping method is disclosed herein, based on laser-based micro-patterning and lamination techniques (Nath et al., *Lab Chip* 10:2286-2291, 2010). In addition to rapid fabrication, a benefit of this technique is the flexibility of the type of materials that can be used. Any materials that can be cut with a laser cutter are available for this fabrication method, which allows the use of multiple biocompatible materials to facilitate manual integration of the HFs.

The inventors have demonstrated the ability to integrate single and multiple HFs into polymeric microfluidic devices using laser patterned plastic sheets/films and lamination. Microfluidic devices integrated with HFs provide new challenges in terms of cell seeding, which was addressed as disclosed herein by developing a cell seeding method based on pressurized flow. The pressurized cell seeding process showed dramatic enhancement of the cell attachment into the lumen of the HFs. Upon the optimization of the cell seeding technique, co-culture of different cell types was demonstrated. Two different formats of co-cultures were possible. In the first configuration one type of cells were cultured inside the lumen and the second type of cells were cultured on the bottom surface of the chamber that holds the HF. Using this configuration simple micro-physiological models can be established to study cell-cell interactions in a microfluidic platform. The second format of co-culture was demonstrated on a more complex HF-integrated system including multiple HFs. Different cells were cultured inside different HFs. Such a system may be utilized to create more complex micro-physiological models that can integrate more than two cell types requiring different specialized media. This system may be applied to study complex interaction between cells to closely mimic in vitro conditions. Furthermore, the demonstrated method can be readily adapted to commercial production schemes with little or no modifications.

The disclosed HF integrated microfluidic devices provide for evaluating the interactions between multiple cell types, as is the case in a tissue or organ. This has previously been challenging because, for example, in vitro cell cultures require very specific culture medium that can promote optimal growth of the tissue. Unlike blood, there are no universal media that can promote optimal growth of different types of cells in vitro. To address these limitations, the typical approach is to mix the optimal media for the individual cell types at a given proportion to carry out the co-culture. This approach typically allows the growth of only a few cell types (e.g., two cell types). Adding more cell types to the co-culture requires the mixing of more growth media and thereby, deviating significantly from the media that the cells are optimized to grow. Recent studies on the cell-cell interaction between mammary epithelial cells and fibroblasts and mammary epithelial cells and fat tissues indicates their role in the breast cancer pathogenesis. However, current in vitro models have been developed with co-culturing only two types of cells and in the absence of the other stromal cells. Similarly, ECM stiffness has also been identified to play a significant role in breast cancers. However, these studies are carried out on in vitro platforms where the stiffness of the ECM is pre-determined by modifying the ECM chemistry. The limitation of this approach is that it is not possible to dynamically change the stiffness on the same set of cells to investigate the outcome, thereby limiting our abilities to perform a complete understanding on how the same set of cells would behave under varying condition. The disclosed devices and methods address these limitations.

I. Terms

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise. All references cited herein are incorporated by reference in their entirety.

Any theories of operation are to facilitate explanation, but the disclosed devices, materials, and methods are not limited to such theories of operation. Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed components and materials can be used in conjunction with other components and materials. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

In some examples, values, procedures, or devices are referred to as "lowest," "best," "minimum," or the like. It will be appreciated that such descriptions are intended to indicate that a selection among many used functional alternatives can be made, and such selections need not be better, smaller, or otherwise preferable to other selections.

Examples are described with reference to directions indicated as "above," "below," "upper," "lower," and the like. These terms are used for convenient description, but do not imply any particular spatial orientation.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

Cell Culture: Growth or maintenance of a population of cells in a defined set of conditions (such as culture medium, extracellular matrix, temperature, and/or time of culture) in vitro. In some examples, cell culture includes growth or maintenance of a substantially pure culture (for example, substantially a single cell type). In additional examples cell culture includes growth or maintenance of a mixed culture, such as co-culture of two or more types of cells. In further examples, cell culture includes growth or maintenance of cells in contact with an extracellular matrix (such as one or more extracellular matrix components).

Culture Medium: A synthetic set of culture conditions (e.g., a fluid) with the nutrients necessary to support the viability, function, and/or growth of a specific population of cells, a tissue, and/or an organ. Culture media generally include components such as a carbon source, a nitrogen source and a buffer to maintain pH. Additional components in culture media also may include one or more of oxygen carriers, hormones, growth factors, protease inhibitors, protein hydrolysates, shear force protectors, proteins, vitamins, glutamine, trace elements, inorganic salts, minerals, lipids, and/or attachment factors.

Exosome: Cell-derived vesicles that are present in fluids (including but not limited to blood, plasma, or cell culture medium) or are associated with extracellular matrix. Exosomes include components from their cell of origin, including protein and/or RNA (such as mRNA and/or miRNA). Exosomes may be involved in cell-cell signaling in some circumstances.

Hollow fiber (HF): A tubular membrane defining a central lumen, an elongated body having an inner and outer surface, and two openings. HFs also include one or more pores capable of allowing fluids, or components contained in fluid, to pass between the central lumen and an environment exterior to the elongated body.

Organ or tissue: A "tissue" includes a structure including cells (such as one or more cell types) that have similar or related structure and/or function. Examples of tissue types include epithelial, neuronal, muscle, endothelial or vascular, breast, and/or connective tissue. An "organ" includes a structure including two or more tissue types that perform one or more particular functions. Exemplary organs include heart, lung, liver, kidney, brain, intestine, stomach, bone, skin, bladder, and pancreas. As utilized herein, "organ" or "tissue" also refers to a microfluidic device that includes two or more cell types and mimics or recapitulates one or more aspects of a tissue or organ, including, but not limited to vascular tissue or breast tissue.

II. Device Embodiments

The disclosed devices include one or more (such as 2 or more, 3 or more, 4 or more, 5 or more, 6 or more, 7 or more, 8 or more, 9 or more, or 10 or more) channels integrated into and extending through a chamber having an upper wall, a lower wall, and at least two (such as at least 2, 3, 4, 5, 6, or more) side walls. In particular embodiments, the devices include two or more channels integrated into and extending through the chamber. Although embodiments of the devices are described herein primarily with respect to hollow fibers, the structures can also include channels of other shapes, including channels with square or rectangular cross-section, or other shapes. In some embodiments, the channel has four sides and at least one side of the channel includes a membrane that allows for fluid communication between the channel and the chamber (for example, a membrane including one or more pores capable of allowing passage of fluids, or components contained in fluid).

Each of the channels has a central lumen, an elongated body having an inner and outer surface and two opening, such as an inlet and an outlet which can be used for fluid flow through the channel. Fluid flow through the channels may be individually managed (e.g., individually addressable) or may be connected to a single fluid input and/or output for multiple channels. The devices also include at least one inlet and one outlet fluidly coupled to the chamber containing the channels, which in some embodiments are in the upper wall of the chamber. In some embodiments of the devices, the upper wall and/or lower wall of the chamber or one or more of the side walls (such as 1, 2, 3, 4, 5, 6, or more side walls) include a flexible substrate and the device further includes an upper chamber and/or a lower chamber. The device may further include one or more vent channels in the side wall(s) of the chamber fluidly coupled to the middle chamber for passage of fluid and/or air into or out of the chamber, for example, during an increase or decrease in pressure in the chamber.

A plurality of channels can be included in the device, with some embodiments comprising 1 to 100 channels or HFs, such as 1 to 75, 1 to 50, or 1 to 20 channels or HFs (for example, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100). In exemplary embodiments, 1, 2, 3, 4, 5, 6, 8, 10, 12, or more channels or HFs are included. In some embodiments, the plurality of channels or HFs are arranged in a parallel orientation to one another and each channel is separated from other channels or HFs by a distance of 0.1 mm to 10 mm (or higher), such as 0.5 to 2 mm, or 1 to 2 mm. In other embodiments, the channels are in a concentric or approximately concentric arrangement (such as one or more concentric rings of channels) and each channel is separated from other channels or HFs by a distance of 0.1 mm to 10 mm (or higher), such as 0.5 to 2 mm, or 1 to 2 mm. The channels can be arranged in a planar or non-planar arrangement, as desired.

Figure 5A:
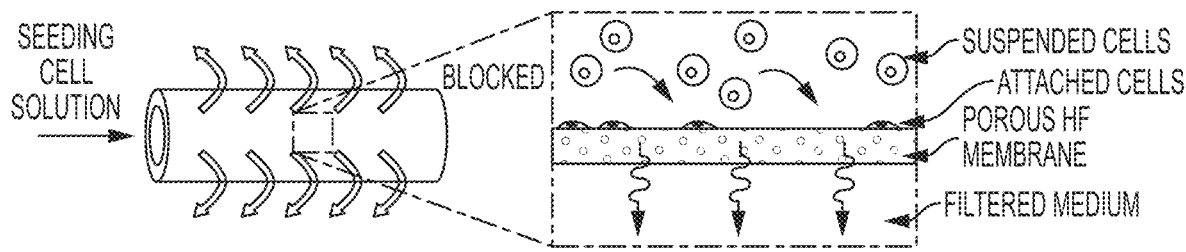
FIGS. 5A-5E are a series of panels showing cell culture in HFs.

HFs are tubular membranes defining a central lumen, an elongated body having an inner and outer surface, and two openings. HFs also include one or more pores capable of allowing fluids, or components contained in fluid, to pass between the central lumen and an environment exterior to the elongated body. In some embodiments, the HFs include a plurality of pores passing from the exterior diameter of the central lumen through the exterior of the elongated body. The pores can have any shape and size sufficient for allowing passage of fluids, cells, chemical compounds, and/or gases into and/or out of the HF. In particular disclosed embodiments, the pore size can range from 0.01 to 3 μm (or higher), such as 0.1 to 1 μm, or 0.2 to 0.4 μm. In exemplary embodiments, the pore size can be 0.2 μm. The pores can have the same or different shape and/or size and any number of pores can be included in each HF. In particular disclosed embodiments, the pores can allow fluid communication between a fluid-fluid interface, as illustrated in FIG. 5A. In some examples, the pores are of a size such that exosomes secreted by cells in the HF can pass into and/or out of the HF. In some embodiments, the channels or HFs can be made of a polymeric material, such as polyethersulphone, mixed cellulose ester, cellulose, polysulfone, polypropylene, polyvinylidene fluoride, and/or other biocompatible polymeric materials. Other channel types (e.g., channels with a square or rectangular cross-section) are configured similarly and include a plurality of pores extending from the central lumen through the inner and outer surface of the channel.

Figure 1B:
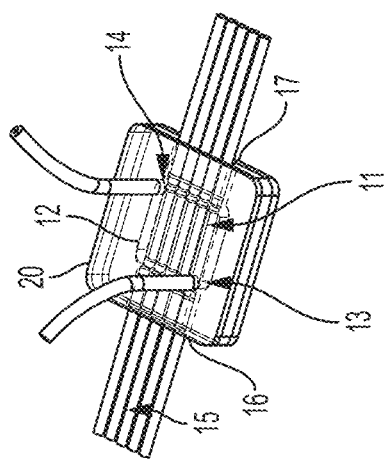
Figure 1A:
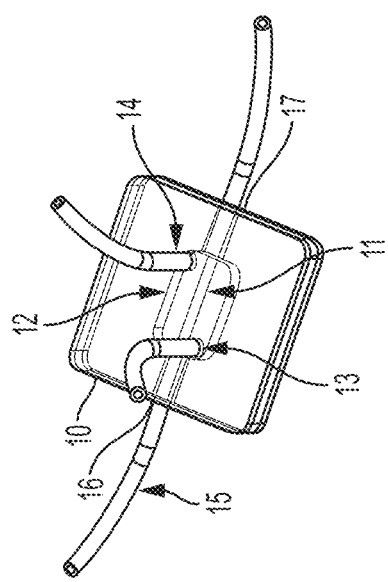
Figures 3A, 3B, 3C:
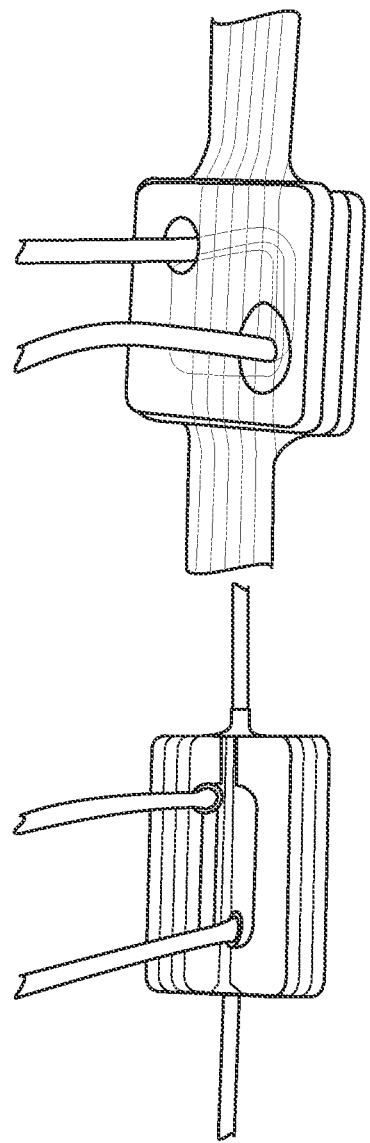
FIGS. 3A-3C are digital images of a single HF integrated device (FIG. 3A), an individually addressable multi-HF device (FIG. 3B), and a multi-HF device with single flow input (FIG. 3C). Scale bar=1 cm.
Figure 4A:
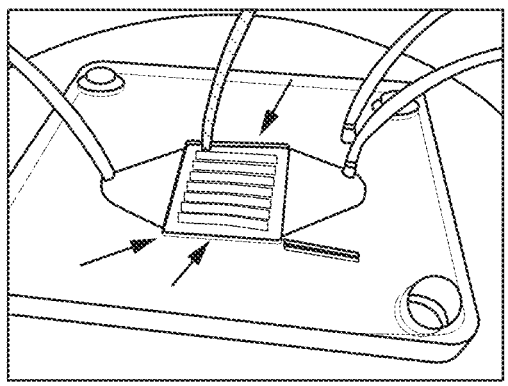
FIGS. 4A-4D are a series of panels showing a design for preventing leakage in multi-HF devices having a single flow input.
Figure 4C:
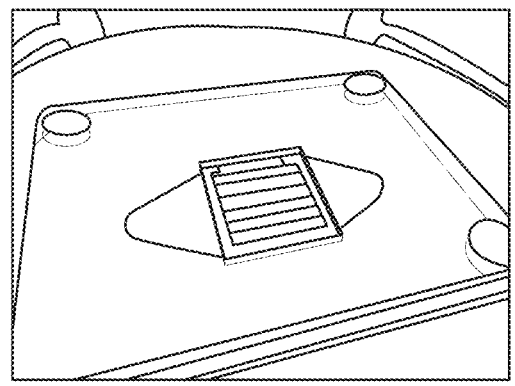
Figure 4B:
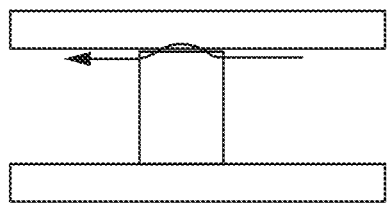
Figure 4D:
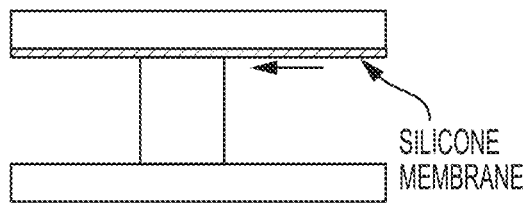

Referring to FIGS. 1A-1C, three exemplary embodiments of disclosed HF integrated devices are illustrated. FIG. 1A illustrates an embodiment 10 with a single HF 11 extending through a chamber 12. The chamber includes an inlet 13 and an outlet 14 fluidly coupled to the chamber for introduction and removal of fluid, hydrogel, and/or air in the chamber. Fluid is passed through the HF through perfusion tubing 15, which is fluidly coupled to an inlet 16 and an outlet 17 of the HF. FIG. 1B illustrates an embodiment 20 with four HFs 11, each with an individually addressable fluid path through separate perfusion tubing 15 for each HF, each with an individual inlet 16 and outlet 17. The four HFs are integrated in a single chamber 12 with an inlet 13 and an outlet 14, as in FIG. 1A. FIG. 1C illustrates an embodiment 30 with four HFs 11 integrated in the chamber and fluidly coupled to two side chambers 18, one on the HF inlet side of the chamber and which includes a side chamber inlet 19 and one on the HF outlet side of the chamber and which includes a side chamber outlet 21. In this embodiment, all of the HFs are perfused with the same medium through a single set of perfusion tubing 15. FIGS. 3A-3C are digital images of exemplary single HF (FIG. 3A), multiple individually addressable HF (FIG. 3B), and multiple HF with side chamber (FIG. 3C) device embodiments, respectively.

Figure 2A:
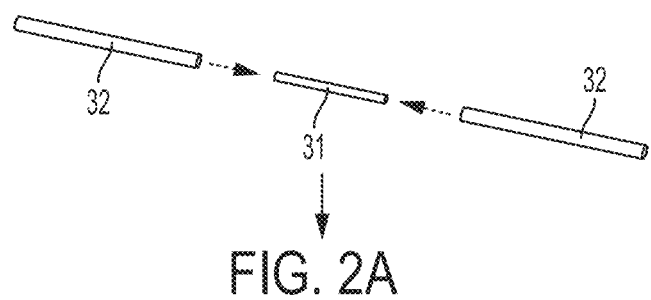
FIGS. 2A-2D are a series of schematic drawings showing fabrication of a single HF integrated microfluidic device. The HF with tubing attached at each end (FIG. 2A) is integrated into a middle layer (including a chamber portion), which is placed on a bottom layer (FIG. 2B). A top layer is added (FIG. 2C) and tubing is connected for providing fluid input and output to the chamber (FIG. 2D).
Figure 2B:
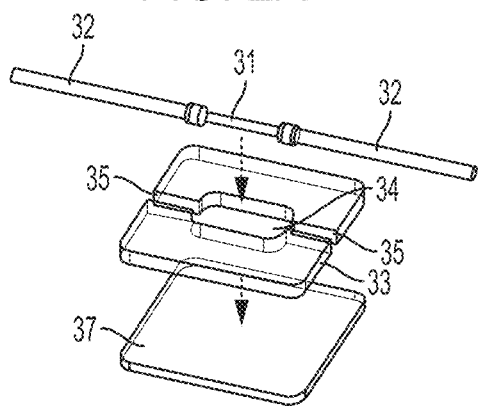
Figure 2C:
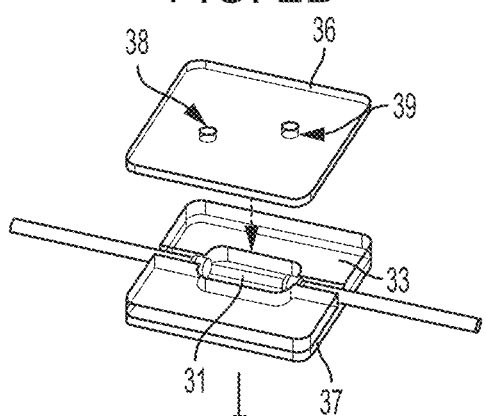
Figure 2D:
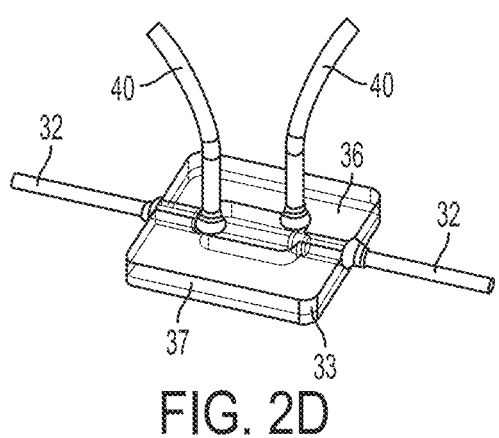

FIGS. 2A-2D illustrates an exemplary method for making some device embodiments. This illustrates a method of making a device with a single HF for the sake of clarity; however, a device with a plurality of HFs (such as two or more HFs) can be made by integrating multiple HFs in the chamber during fabrication. As illustrated in FIG. 2A, a HF 31 is connected at each end to perfusion tubing 32 (e.g., silicone tubing), for example by fastening or connecting the tubing to each end of the HF. As shown in FIG. 2B, the middle layer 33 is fabricated by cutting in a solid substrate (such as ⅟₁₆" acrylic sheet) a chamber 34 with a channel 35 at each end to accommodate the HF and perfusion tubing. The HF and perfusion tubing are placed in the middle layer (FIG. 2C). Top 36 and bottom 37 layers are fabricated from a solid substrate (for example, including at least one inlet 38 and at least one outlet 39 in the top layer, which is fluidly connected to the chamber) and are laminated to the middle layer (FIG. 2D). In one example, the top layer and bottom layer are laminated to the middle layer using adhesive transfer tape; however, other means of laminating the layers can also be used. The HF and perfusion tubing assembly can be sealed to the device by applying adhesive (such as medical grade silicone glue). Tubing can also be connected to the chamber inlet and outlet and sealed by applying adhesive.

Figure 10:
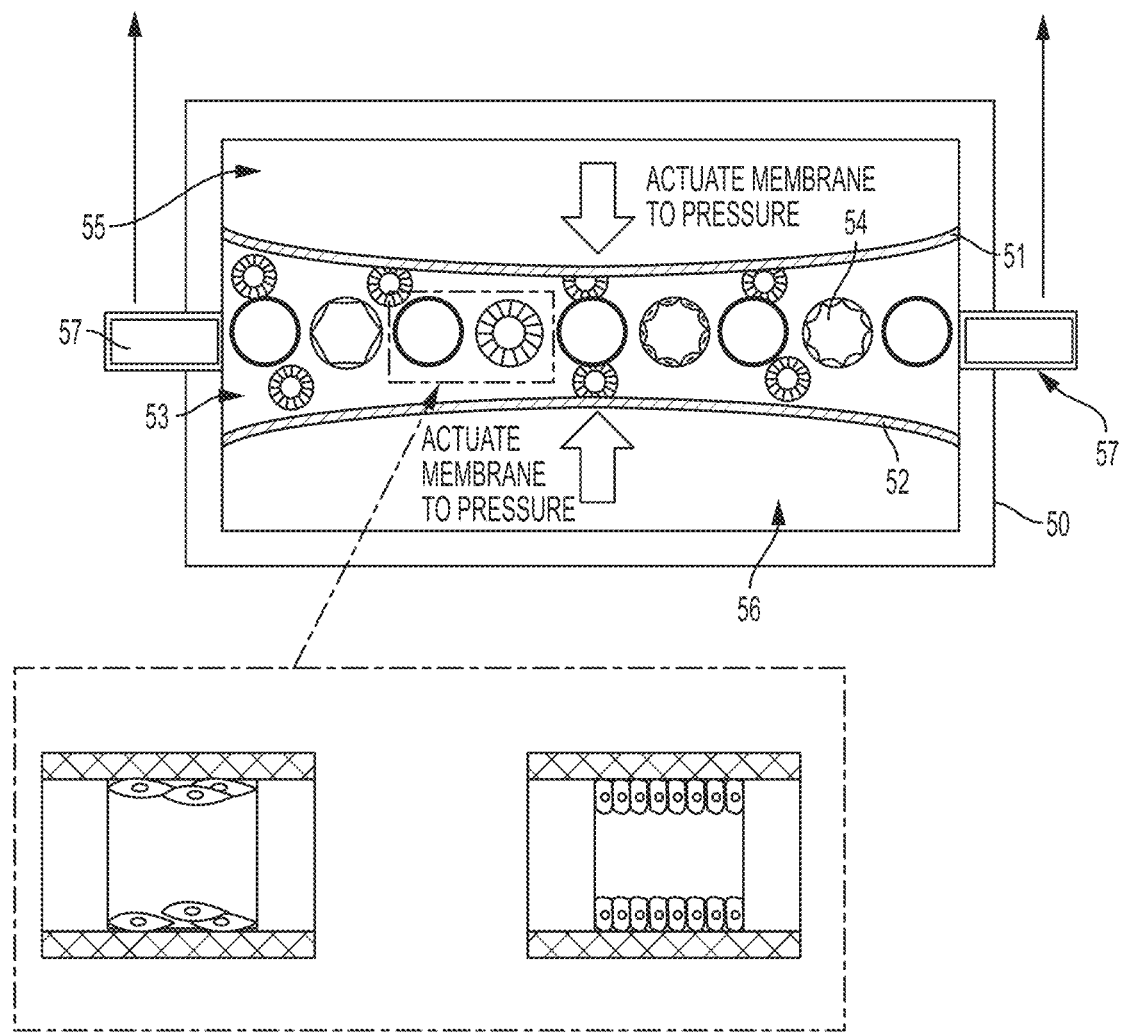
FIG. 10 is a schematic diagram showing a cross-section of the device shown in FIG. 8 when the flexible membrane above and below the chamber is actuated to apply pressure to the matrix. The hollow fibers may alternatively be replaced with channels of other shapes, such as rectangular channels (inset).

In some embodiments, the disclosed devices include one or more flexible substrates (for example, placed above and/or below a chamber housing one or more HFs) that permits modulation of pressure in the chamber. FIG. 10 illustrates a cross-sectional view of one device embodiment 50. In this embodiment, the upper wall 51 of the chamber and the lower wall 52 of the chamber 53 are a flexible substrate (such as a silicone membrane). In this embodiment, the device includes the chamber 53 (containing HFs 54, and in some embodiments, a matrix), an upper chamber 55 in contact with the upper wall or top of the chamber and lower chamber 56 in contact with the lower wall or bottom of the chamber, which are air- or fluid-filled and include means for modulating the pressure in the chambers. In some examples, each of the upper chamber and lower chamber include at least one port (not shown) (e.g., at least one inlet or outlet) that is fluidly coupled to the exterior environment. The port can be used to increase the pressure in the upper and/or lower chamber, for example, by increasing air or fluid pressure and thereby deforming the upper and/or lower wall of the chamber into (e.g., towards the center of) the chamber to increase pressure in the chamber. At least one side wall of the middle chamber also includes one or more vent channels 57 (in this example, one vent channel on each of two opposite walls of the chamber is shown), such as a fluid outlet. The vent channel(s) may include an integrated filter (e.g., a 0.2 μm filter; not shown). The vent channel(s) permit fluid and/or air to exit the chamber when pressure is applied to the flexible upper wall and/or lower wall of the chamber.

Figure 11:
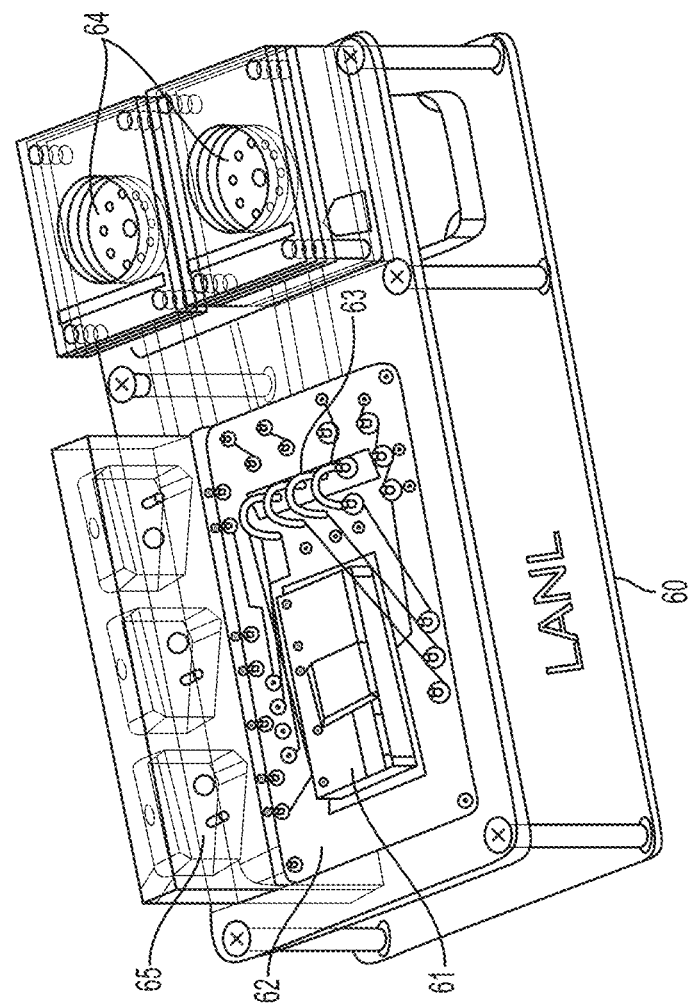
FIG. 11 is a schematic showing the flow diagram to manage fluid flow in the system shown in FIGS. 8-10 (left) and a schematic drawing of an integrated flow management system with a planar HF integrated microfluidic device (right).
Figure 11:
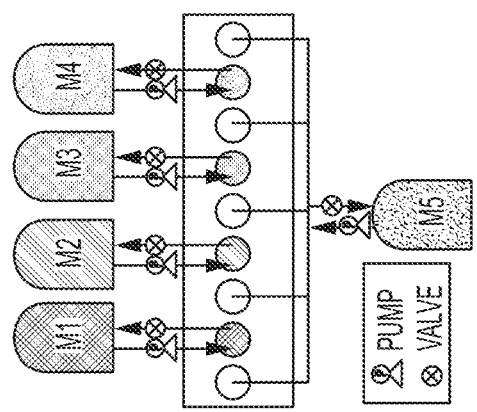

In some embodiments, the disclosed microfluidic devices are integrated in a microfluidic system including one or more of pumps, valves, reservoirs, channels, or other components for fluid management. Exemplary systems including these components and that could be modified to integrate the disclosed devices are disclosed in International Patent Publication Nos. WO 2016/049363 and WO 2016/049365 (incorporated herein by reference). Referring to FIG. 11, in one embodiment the system 60 includes a device with a planar configuration 61 coupled to a fluid circuit board 62. The fluid circuit board includes valves 63 for flow switching and management of fluid flow to the chamber and HFs of the device, and the system also includes one or more pumps 64 fluidly coupled to the fluid circuit board, and one or more reservoirs 65 fluidly coupled to the pump(s).

Figure 12:
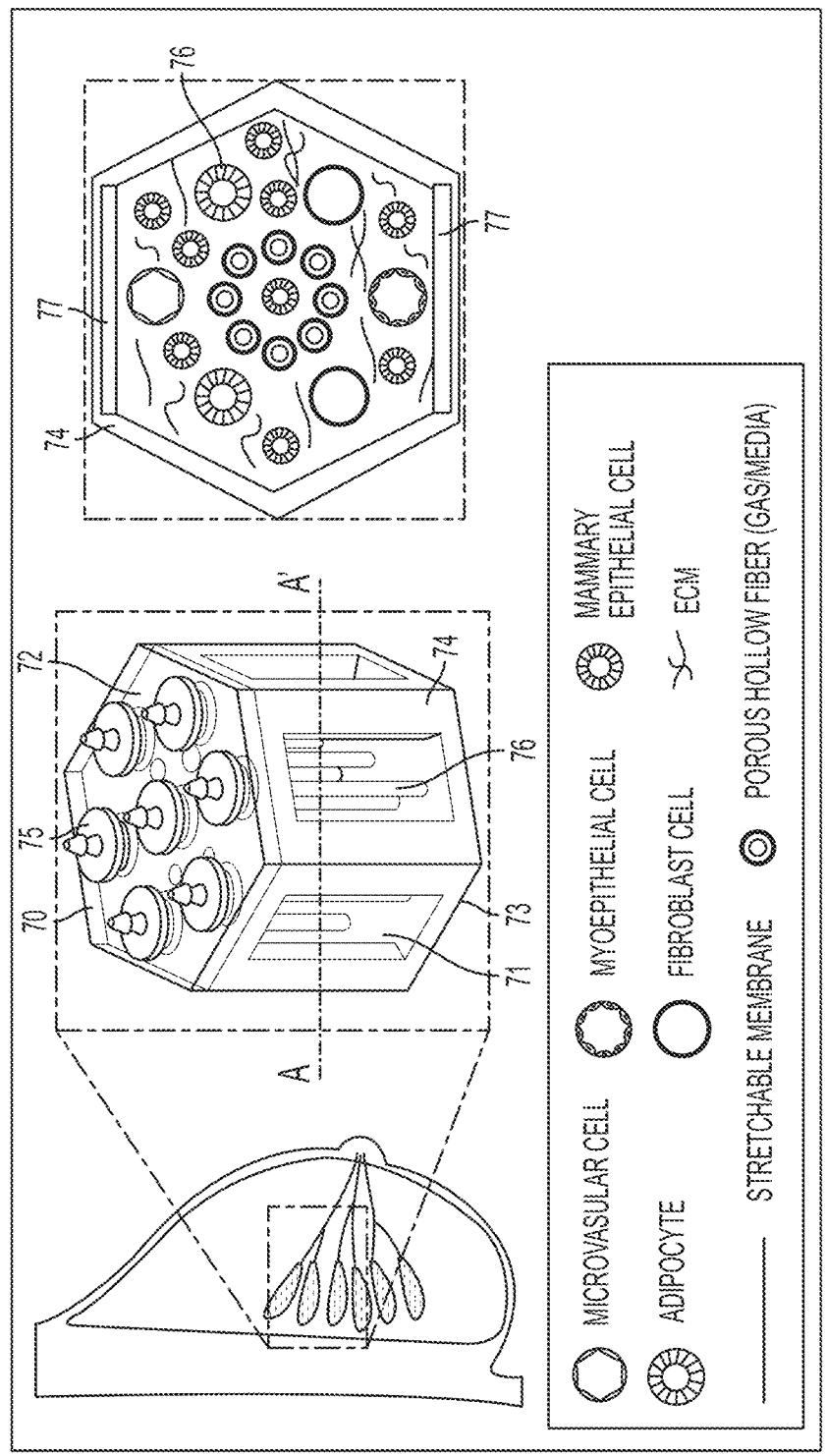
FIG. 12 is a schematic diagram of an alternative HF integrated microfluidic device embodiment, which can be used for modeling breast tissue microenvironment (left and center). The device is hexagonal in shape and includes two sets of HFs in a concentric cylindrical orientation (shown in cross-section, right). The outer set of HFs is seeded with stromal cells (such as microvascular cells, adipocytes, myoepithelial cells, and/or fibroblasts). The inner set of HFs is used to perfuse media into the chamber. The chamber is seeded with mammary epithelial cells and can be filled with hydrogel matrix.
Figure 13:
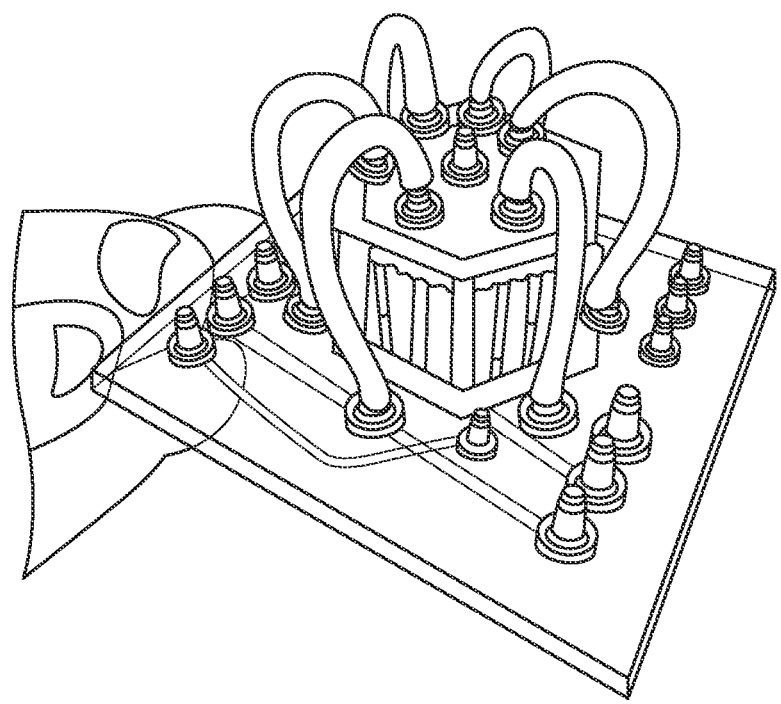
FIG. 13 is a digital image of an exemplary hexagonal HF microfluidic device embodiment, including individual tubes for perfusing medium to/from isolated reservoirs (not shown) for each stromal cell type shown in FIG. 12.

Referring to FIG. 12, an alternative device embodiment 70 is illustrated. This embodiment includes a chamber 71 with a top 72, bottom 73, and six sides 74. The top of the chamber includes fluid inlets 75 coupled to HFs 76 that are vertically arranged in and extend through the chamber. As shown in the cross-sectional view (right), the chamber 71 includes multiple HFs 76, which in this embodiment are arranged in concentric rings in the chamber. In this exemplary embodiment, the device includes an outer ring of HFs (which can be seeded with cells, such as one or more cell types) and an inner ring of HFs, which are not seeded with cells and can be used to perfuse the chamber. The chamber can be filled with a matrix (such as a hydrogel or other extracellular matrix) and may also include one or more cell types. One or more of the sides of the chamber (for example, two opposite sides of the chamber) include a flexible membrane 77.

Figure 14:
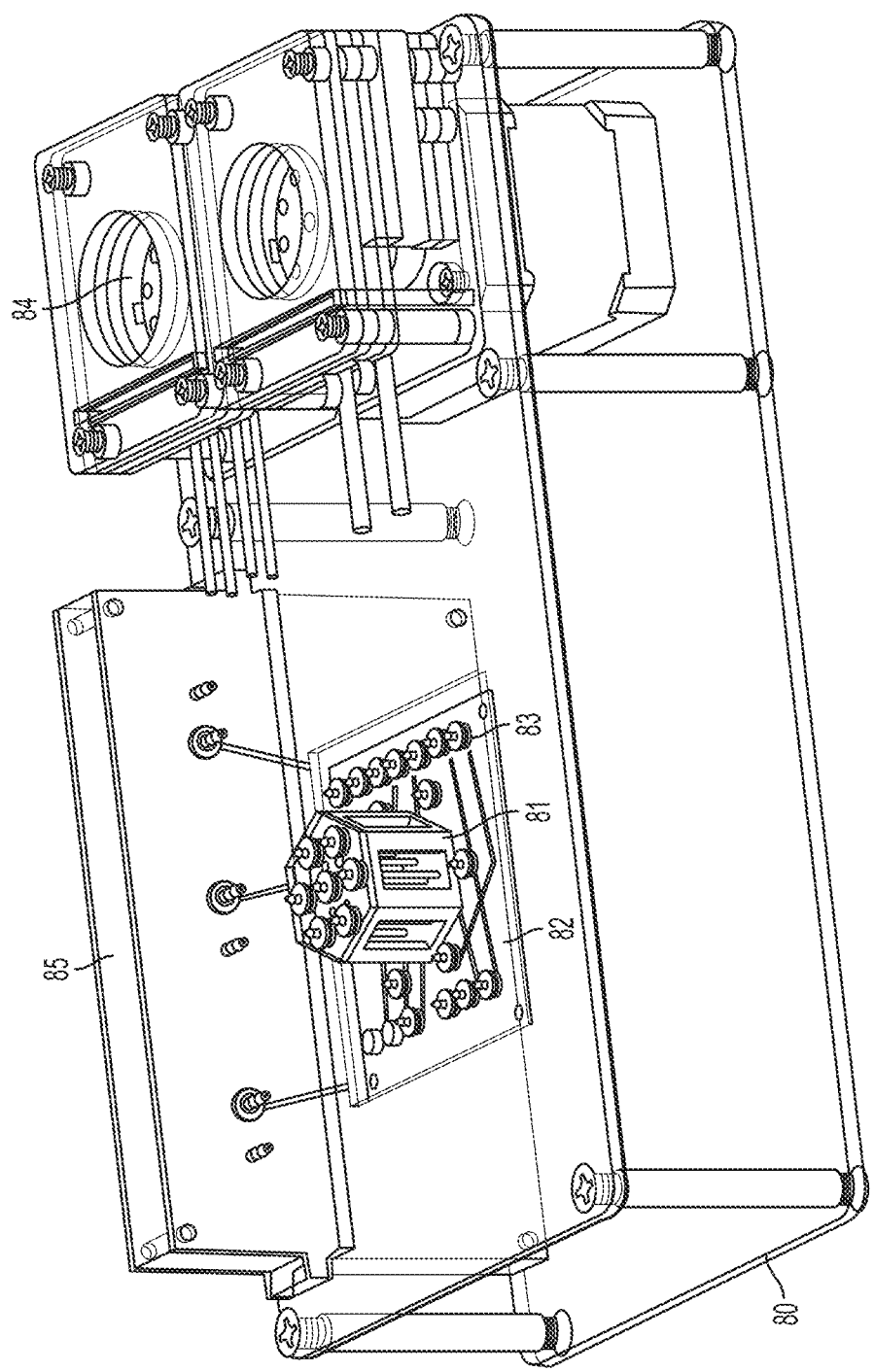
FIG. 14 is a schematic diagram showing an integrated flow management system for the device shown in FIGS. 12 and 13.

Referring to FIG. 14, in one embodiment the system 80 includes a device with a vertical, hexagonal configuration 81 coupled to a fluid circuit board 82. The fluid circuit board includes valves 83 for flow switching and management of fluid flow to the chamber and HFs of the device, and the system also includes one or more pumps 84 fluidly coupled to the fluid circuit board, and one or more reservoirs 85 fluidly coupled to the pump(s).

Figure 15:
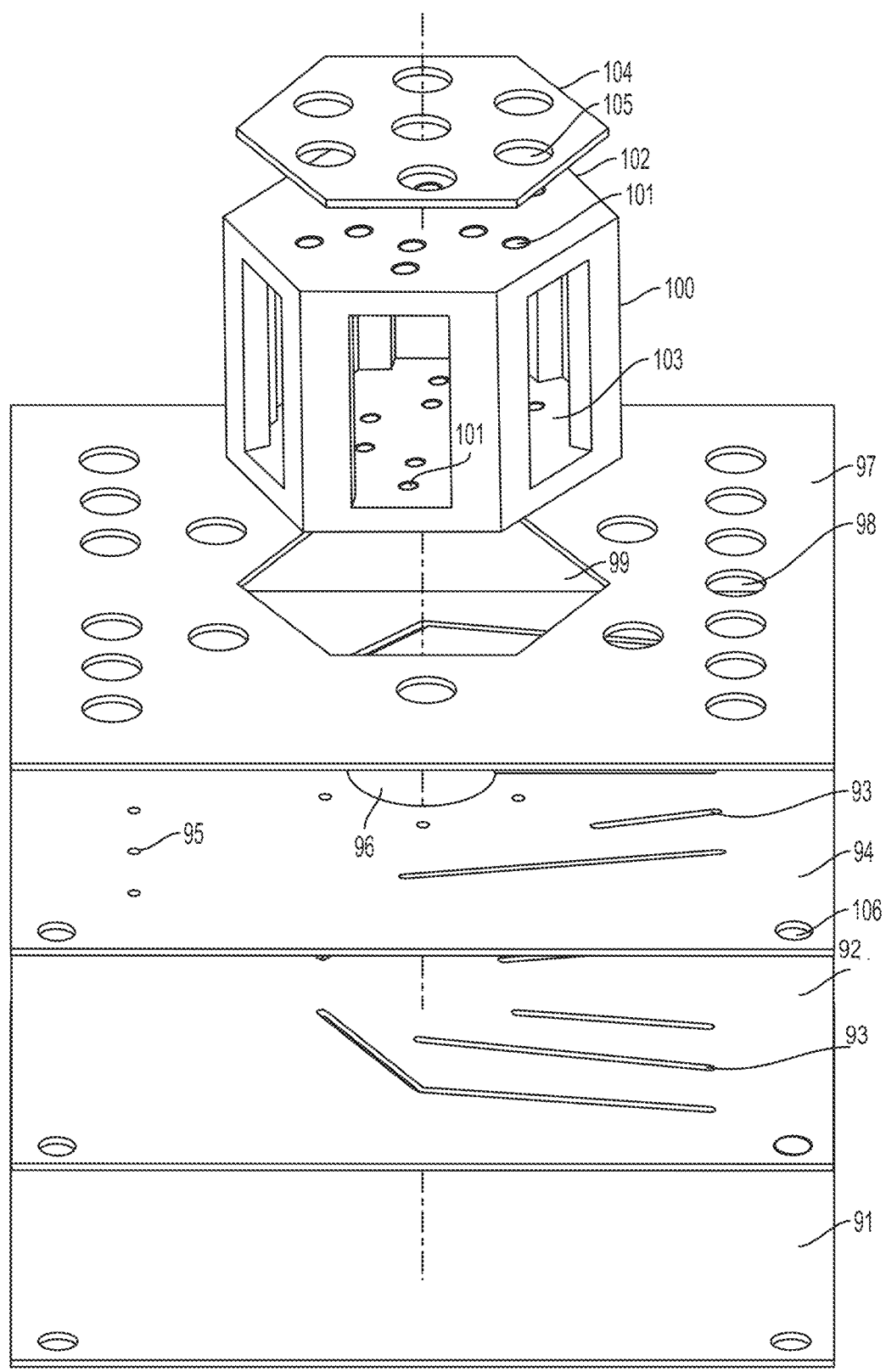
FIG. 15 is an exploded view of an exemplary vertical (and hexagonal) configured HF microfluidic device embodiment.

FIG. 15 shows an exploded view of a device embodiment that could be coupled to a fluid circuit board, such as that shown in FIG. 14. The device includes a bottom 91, a first layer 92 including channels 93 for fluid flow (e.g., from a fluid circuit board). A second layer 94 includes channels, openings 95 for fluid communication between the layers, and an opening 96 for fluid communication with the chamber. The third layer 97 includes openings 98 for fluid communication with one or more ports and/or valves (not shown) and a base 99 for insertion of the chamber 100, which includes corresponding openings 101 on the top 102 and bottom 103 of the chamber for insertion of HFs (not shown). A lid 104 is on top of the chamber and includes openings 105 that align with openings in the chamber where the HFs are inserted. The openings in the lid are fluid inlets that are coupled to one or more HFs, for example by insertion of ports and/or tubing (not shown). At least some of the layers of the device include alignment holes 106, which can be used in assembly to align the portions of the device.

III. Methods of Co-Culturing Cells in Microfluidic Devices

Methods of co-culturing two or more cell types in the microfluidic devices and systems disclosed herein are provided. The methods include culturing two or more (such as 2, 3, 4, 5, or more) cell types in one of the disclosed devices or systems. In some embodiments, the methods include culturing at least two different cell types in separate HFs or channels in the device. In other embodiments, the methods include culturing at least one cell type in an HF or channel in the device and at least one cell type in the chamber containing the HF or channel (e.g., either on the surface of the chamber or embedded in a matrix filling the chamber). Additional embodiments include combinations of these methods.

Culturing the cells includes incubating the cells under appropriate conditions for cell survival, growth, and/or differentiation. Such conditions include appropriate temperature (e.g., about 35-39° C., such as about 37° C.) and atmosphere (such as about 5% $CO_2$ in air). Such conditions also include contacting the cells with a culture medium that supports survival, growth, and/or differentiation of the cells. One of ordinary skill in the art can select appropriate cell culture media, depending on the cell(s) being cultured. In some examples, the methods include contacting cells with a culture medium by flowing culture medium through a HF or channel including cells (such as a HF with cells adhered to the inner surface). In additional examples, the methods include contacting cells with a culture medium by flowing culture medium through a chamber of the disclosed devices. In further examples, the methods include contacting cells with a culture medium by flowing culture medium through a HF or channel that does not contain cells. The culture medium passes out of the pores in the HF or channel into the chamber containing the HF or channel. In some examples, the chamber contains fluid (such as a culture medium), while in other examples, the chamber contains a hydrogel matrix (such as Matrigel® matrix). Culture medium can be flowed through the HFs and/or chamber using a pump (such as a syringe pump or a peristaltic pump).

The methods include culturing at least one cell type in at least one HF or channel in a device or system disclosed herein. Cells are introduced into a HF or channel by introducing a fluid (such as a cell culture medium) containing the cells into the HF or channel and allowing the cells to attached to the inner surface of the HF of channel. An exemplary method is illustrated in FIG. 5A. A cell seeding solution containing cells suspended in a culture medium is introduced into the lumen of a HF at one end. The opposite end of the HF is closed (e.g., with a plug or clamp) to prevent the cell seeding solution from draining from the HF. In some examples, the cell seeding solution is introduced to the HF at ambient pressure (referred to herein as "static" seeding). In other examples, the cell seeding solution is introduced to the HF using fluid flow (e.g., using a syringe pump). This forces the solution out of the HF through the wall of the HF and the cells are seeded onto the inside wall of the HF (FIG. 5A, referred to herein as "pressurized" seeding). In one example, the pressurized seeding method uses a flow rate of 0.5 mL/min for 20 seconds. Following seeding, the HF is incubated for a period of time for the cells to adhere to the inner surface of the HF for example, at least 5 minutes, at least 10 minutes, at least 15 minutes, at least 30 minutes, at least 1 hour, at least 2 hours, at least 4 hours, at least 8 hours, at least 12 hours, at least 16 hours, at least 24 hours or more (such as 5-60 minutes, 30-90 minutes, 1-4 hours, 2-8 hours, 6-16 hours, 12-24 hours or more). Once the cells are seeded, the method includes circulating cell culture medium (for example, a cell culture medium specific for the cells seeded) through the HF from a medium reservoir. In some examples, the medium is continuously circulated, with replacement of the medium periodically (for example, every day, every 2 days, every 3 days, every 4 days, every 5 days, every 6 days, every 7 days, or more). In other examples, the medium is continuously circulated with a portion of the medium (such as 10-50% of the medium) replaced with fresh medium periodically. In further examples, fresh medium is constantly supplied from a medium reservoir, and is discarded after following through the HF.

Figure 6A:
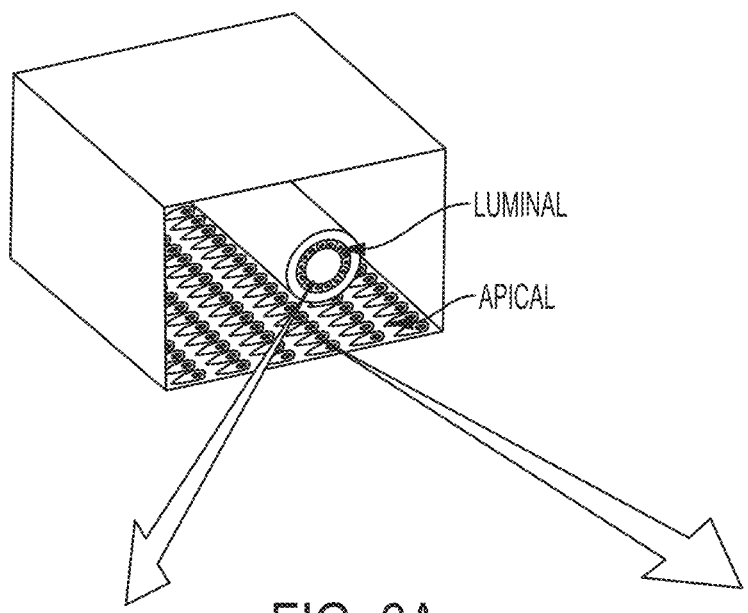
FIGS. 6A-6C are a series of panels showing co-culture of cells in a single HF integrated device.

As illustrated in FIG. 6A, in some embodiments, the disclosed methods include culturing one cell type in the lumen of a HF and culturing one cell type in the chamber housing the HF. In other embodiments, the methods include culturing one cell type in a plurality of HFs in a single device and culturing one cell type in the chamber housing the plurality of HFs. In an additional embodiment, the methods include culturing at least two different cell types in individual HFs in a single device and culturing one cell type in the chamber housing the plurality of HFs. In any of these embodiments, the cell type(s) in the HFs may be the same or different than the cell type in the chamber.

Figure 7A:
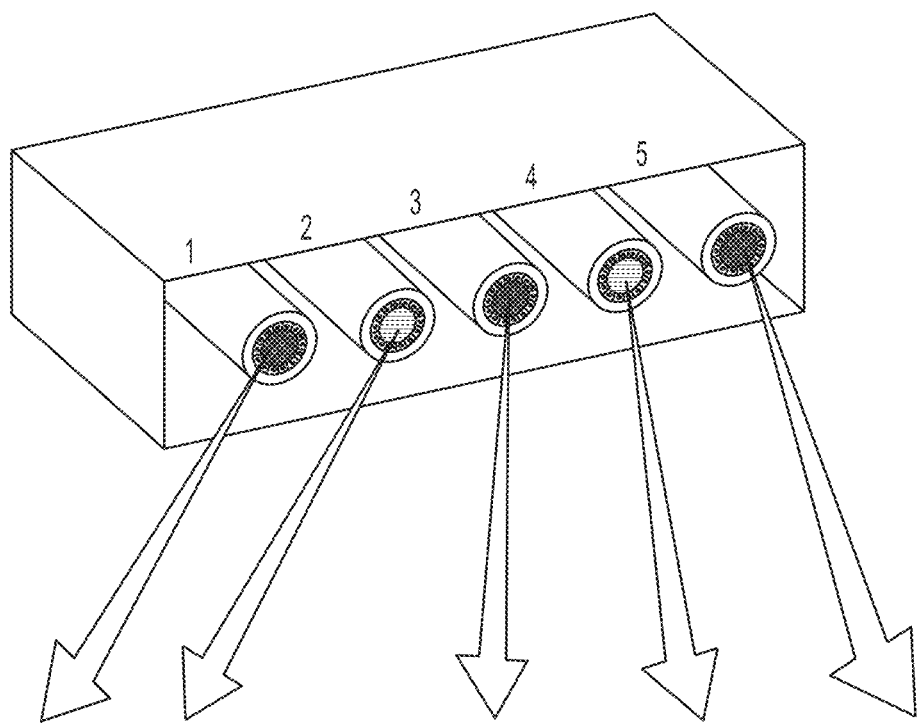
FIGS. 7A and 7B are a series of panels showing co-culture of cells in a multiple HF integrated device.

As illustrated in FIG. 7A, in some embodiments, the disclosed methods include culturing two or more cell types in the lumen of individual HFs in a single device. In one example, the device includes two or more HFs (such as 2, 3, 4, 5, 6, 7, 8, 9, 10, or more HFs) and at least two of the HFs include different cell types.

In additional embodiments, the methods include culturing three or more cell types (such as 2, 3, 4, 5, or more cell types) in a disclosed device. In some examples, the method includes culturing different cell types in individual HFs and optionally also culturing one or more cell types in the chamber, for example in a hydrogel matrix (e.g., Matrigel) in the chamber. In some examples, the method includes perfusing the matrix with medium by passing cell culture medium through a set of HFs in the chamber, wherein the HFs do not include cells. In some examples, the method includes culturing different cell types in individual HFs and optionally also culturing one or more cell types in the chamber, for example on the bottom surface of the chamber. In some examples, the method includes contacting the cells in the chamber with a fluid (such as a cell culture medium).

Figure 8:
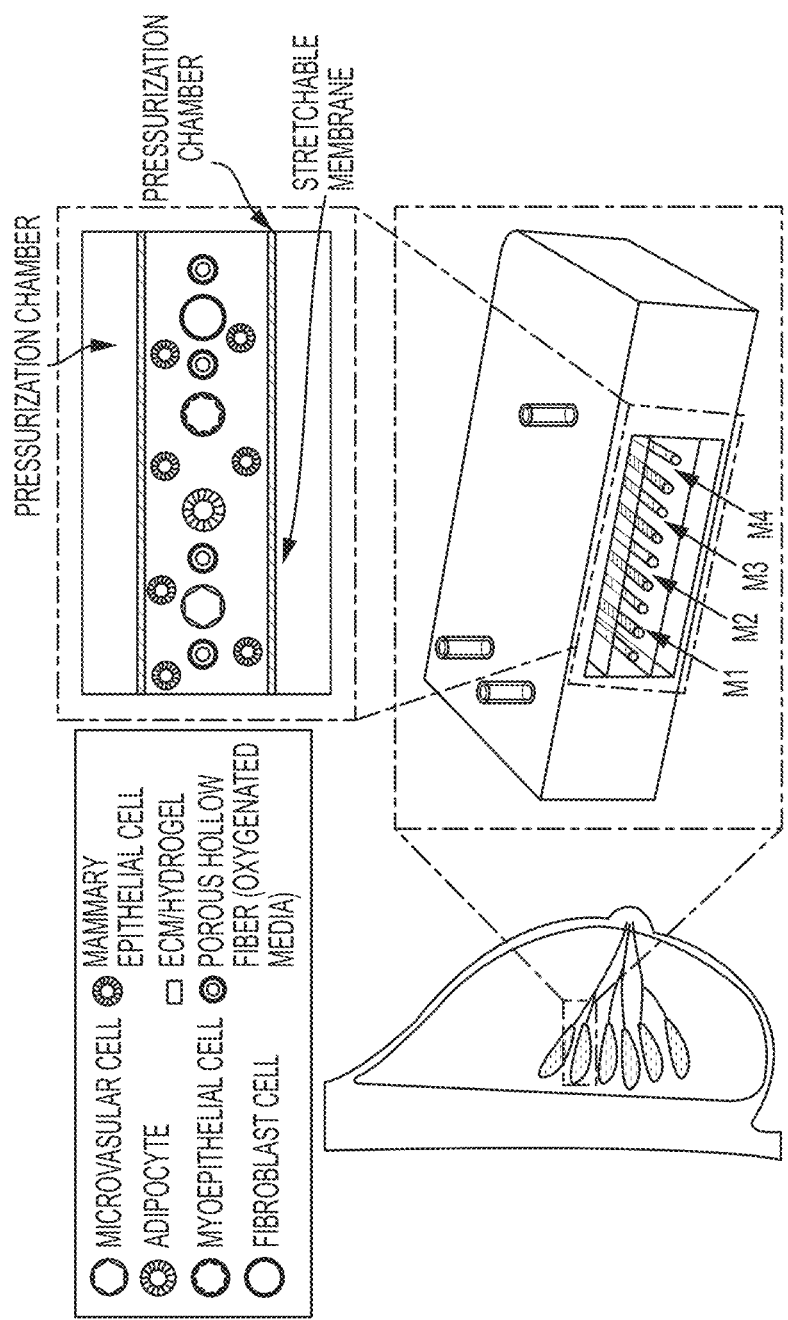
FIG. 8 is a schematic diagram of an exemplary HF integrated microfluidic device for modeling breast tissue microenvironment. The device includes two sets of HFs, one set seeded with cells and perfused with cell culture medium appropriate for the particular cell type (M1, M2, M3, M4) and the other set for perfusion of the matrix between the fibers with a common medium (porous HF (oxygenated media)). Inset, schematic diagram showing a cross section of the device in an embodiment for culturing the indicated cell types.

In some examples, the method includes culturing at least five different types of cells in a disclosed device. As illustrated in FIG. 8, in one specific example, the method includes culturing microvascular cells in one HF, adipocytes in another HF, myoepithelial cells in another HF, and fibroblast cells in another HF, and mammary epithelial cells (such as normal mammary epithelial cells or mammary tumor cells) in a hydrogel matrix in the chamber containing the HFs. Each HF is perfused with cell culture medium appropriate for the cell type in the HF and the cells in the hydrogel matrix are perfused with cell culture medium by passing an appropriate medium through one or more separate HFs that do not contain any cells (and therefore allow the medium to pass into the matrix through the pores in the HF). FIGS. 8-10 and 12 illustrate embodiments for modeling breast tissue or breast cancer that include multiple breast-specific cell types; however, the disclosed methods can be utilized with combinations of cell types to model any tissue or disorder. For example, in one non-limiting example, the disclosed devices and methods can be used to model other types of cancer, including but not limited to prostate cancer.

In additional embodiments, the methods also include modulating the stiffness of the matrix surrounding the channels and any cells in the matrix. The stiffness of the matrix is modulated by applying pressure to a flexible membrane above and/or below the chamber containing the channels and the matrix. This reduces the water content of the matrix (which is removed through one or more vent channels in the device) and increases compression, thereby increasing stiffness.

In some embodiments, the disclosed methods also include analyzing one or more characteristics of the cells in the device. One such characteristic includes viability or survival. Methods of determining cell viability or survival are known to one of skill in the art and include live/dead staining (e.g., LIVE/DEAD Viability/Cytotoxicity Kit, Life Technologies), trypan blue staining, Crystal Violet staining, [$^3$H] thymidine uptake, MTT assay, or others. Another characteristic is a metabolic profile of the cells. Metabolite profiles can be assessed using clinical chemistry analysis tools (e.g., iSTAT (Abbott Laboratories) or Piccolo (Abbott Laboratories)) or mass spectrometry based assays (such as liquid chromatography-mass spectrometry (LC-MS)). Other characteristics includes protein or RNA expression by the cells. In additional examples, exosomes secreted by the one or more cell types are isolated and analyzed. For example, the contents of exosomes can be analyzed to detect proteins and/or RNAs. Methods of detecting and analyzing proteins, RNA, and miRNA are known to one of ordinary skill in the art. The effect of changing conditions, including presence of varying cell types, matrix stiffness, oxygen perfusion, or exposure of one or more cell types to a drug or drug candidate can be analyzed using the disclosed methods.

EXAMPLES

The following examples are provided to illustrate certain particular features and/or embodiments. These examples should not be construed to limit the disclosure to the particular features or embodiments described.

Example 1

Fabricating and Integrating Hollow Fibers in Microfluidic Devices

Methods

Typical bioreactors that integrate HFs are composed of three primary components: (i) HFs; (ii) a chamber that houses the HFs, and (iii) two side compartments. The HFs are exposed to the side compartments in such a way that fluids from these compartments are able to flow through the lumen of the HFs. Fluid in the housing side provides flow on the outer side of the HFs establishing a mass transfer path between the two fluids through the pores of the HFs. Miniaturization of HF bioreactors into a microfluidic platform can lead to channel dimensions that are in the order of a single or a few HFs. Miniaturized HF-integrated bioreactors that have different configurations to allow maximum flexibility of operation were designed.

The first design is composed of a single HF integrated into a planar chamber. In this design the side compartments of a typical HF bioreactor were eliminated, since the single HF could be directly connected to a tube for flow (FIG. 1A). The second and third configurations were composed of multiple HFs to allow for a higher surface area. In the second design each of the HFs were individually addressed by connecting them directly to separate feed tubes and does not have the side chambers (FIG. 1B). The third configuration was designed with side compartments such that multiple HFs were connected to a single fluid input simultaneously (FIG. 1C).

For fabrication, a rapid prototyping method was used based on laser-based micro-patterning and lamination techniques (Nath et al., Lab Chip 10:2286-2291, 2010). FIGS. 2A-2D shows the different layers and materials used to assemble the single HF integrated bioreactor. The top and the bottom chamber were made with $\frac{1}{16}$" acrylic sheet (Plaskolite Optix, Columbus, Ohio). The middle layer was composed of the same acrylic sheet but with laminated adhesive transfer tapes (9122, 3M Company) on both sides. The patterns for each layer were designed using Solid Edge 2D Drafting ST4 software (Siemens PLM Software). The resulting designs were cut using a $CO_2$ laser cutter (M-360, Universal Laser Systems). The components of the device were then cleaned by sonication in distilled water for 10 minutes and dried in a stream of compressed air to remove the burn residues generated by the laser cutting process.

Biocompatible mixed cellulose ester (ME) HFs (pore size 0.2 μm; lumen size 0.6 mm, Spectrum Labs, Rancho Dominguez, Calif.) were cut to the length of 1 cm. Both sides of the HFs were inserted in high-purity silicone rubber tubing (0.030 inch I.D., 0.065 inch O.D., 0.018 inch wall, McMaster-Carr). Medical grade silicone glue (A-4100 RTV, Factor II) was applied to seal the connection (FIG. 2A).

After preparing all of the components, they were manually assembled to obtain the final bioreactor. The middle layer was first bonded to the bottom layer. The HF component was then placed into a slot that was patterned by the laser cutter on the middle layer (FIG. 2B). The top layer was then bonded to enclose the chamber to house the HF assembly (FIG. 2C). Medical grade silicone glue was used to seal the HF/silicon tube assembly from the sides. The top acrylic layer was designed to have access holes to establish inlet and outlet connections to the chamber that houses the HF (FIG. 2C). Silicone tubing was inserted into these access holes and glued to complete the fabrication process (FIG. 2D). A similar approach was utilized to fabricate the other two designs of the HF bioreactors that contain multiple HFs.

Results

The primary purpose of a HF integrated microfluidic platform is to create a two-liquid interface microenvironment for cell cultures. The assembly process described above allowed for the simple fabrication of HF integrated microfluidic devices through the use of stacked planar components and commercially available HFs. Laser based microfabrication precisely develops the mini/micro patterns in biocompatible polymeric substrates (e.g., acrylic, polycarbonate, and the adhesives). FIGS. 3A-3C shows digital images of the HF integrated microfluidic platforms with three different configurations. Modulating the volume and location of the flow chamber allows the flow patterns to be precisely adjusted for a given application. The use of pressure-sensitive tapes to assemble the different layers eliminated the need for specific equipment for bonding. Unlike PDMS-based platforms, this method does not require a mold, allowing rapid opportunity for design modification that is typically necessary at any early stage device development process. Since the process involved manual insertion of the HFs into the assembly, it was important to prevent leakage along the insertion points. For single HF or individually addressed multi-HF devices the HF component was sealed by applying glue at the insertion points. However, for multi-HF systems with single fluid input, some leakage occurred between top and middle layers, near the holder that was used to place multiple HFs. It was not possible to access the holder to apply glue to stop the leakage. Therefore, by adding layers of laser patterned silicone membrane onto the top and the bottom plates, it was possible to prevent the leakage (FIGS. 4A-4D)

Individual fluid flow systems can be established through the different parts of the devices (e.g., inside the HFs and in the outside chambers) by connecting them to any commercial circulation and pumping systems to manually or automatically control the flows for long-term culture. The platforms are suitable for sterilization with alcohol, washing, cell seeding, and long-term incubation. Furthermore, a device with multiple channels connecting independent HFs allowed simultaneous testing of various co-culture conditions. Each HF can be connected to a different flow system to regulate the individual microenvironment relative to neighboring conditions. The flow rates inside and outside the HFs can also be easily tuned with a multi-channel pump using varying flow rates.

Example 2

Cell Seeding and Culture in Hollow Fiber Microfluidic Devices

Methods

Cell Seeding in HF Bioreactors:

Prior to the seeding process, HF embedded devices were sterilized using 70% ethanol wash and overnight UV irradiation at 254 nm. The devices were then washed and rinsed with phosphate buffered saline (PBS, Life Technologies). After the washing process, cell culture medium was injected into the device to replace the remaining PBS. For the single HF bioreactor, human alveolar basal epithelial cells (A549, ATCC) were used. A549 cells were first cultured in a 2-D cell culture plate with DMEM culture medium (Life Technologies) containing 10% FBS (Life Technologies) and 100 U/mL of penicillin-streptomycin (Life Technologies). After 3-5 days, when the culture reached 60-80% confluence, the cells were re-suspended in culture medium using trypsin-EDTA (0.25%, Life Technologies). The cell stock was diluted with culture medium to $2 \times 10^5$ cells/mL. Diluted cell solution was then aspirated using a 1 mL syringe (BD Biosciences). The inlet of the device (HF port) was connected to a syringe through a blunt needle, and the flow rate of the syringe was controlled with syringe pumps (SPL, World Precision Instruments). The cell seeding protocol was composed of two major steps. First, the HF was filled with cell seeding solution and the outlet tubing was closed using Luer lock plugs (FIG. 5A). Second, the cell seeding was initiated by starting the syringe pump at flow rate of 0.5 mL/min for 20 seconds. Under this condition, cells were seeded into the inside wall of the HFs as the solution is forced to pass through the HF walls (FIG. 5A). After the cells were seeded, the HF integrated device was placed at 37° C. in a 5% $CO_2$ incubator for at least 16 h to ensure that the cells adhered to the HF.

Medium was then continuously circulated into the system using the inlet tubing (chamber port) of the device, which was connected to a medium reservoir (5 mL). To maintain the growth of cells, the flow rate in the outside chamber was adjusted to 10 μL/min. The cell culture medium was replaced every week.

Co-Culture in HF Bioreactors:

Co-culturing multiple cell types may require significantly different fluid management protocols including different seeding conditions and multiple media. The ability to perform co-culture of cells inside the HF-integrated microfluidic platforms using two configurations (FIGS. 6A and 7A) was investigated. For both methods, cells were co-cultured for 5 days. The devices were then sacrificed and live-dead staining was performed to measure the cell viability under the given co-culture configurations.

Single HF Devices:

After sterilization of the single HF device, human lung microvascular endothelial cells (HLMVEC, Cell Applications) were seeded on the bottom surface of the outside chamber and human bronchial epithelial cells (BEAS-2B, ATCC) were seeded inside the HF (FIG. 6A). Before seeding, the seeding regions were coated with 30 μg/mL of fibronectin (BD Biosciences) and 50 μg/mL of collagen type I (rat tail, BD Biosciences) for the region growing the HLMVE and BEAS-2B, respectively. The coated bioreactor was incubated at 37° C. for 1 hour and washed with PBS. The cell culture medium was injected into the device to replace the remaining PBS. On the chamber side, which was seeded with HLMVECs, the PBS was replaced with microvascular endothelial cell growth medium (Cell Applications) containing 100 U/mL of penicillin-streptomycin. For the luminal side of the HF, which was seeded with BEAS-2B cells, the medium was changed to bronchial epithelial cell growth medium (Lonza).

Multi-HF Devices:

With the multi-HF integrated devices, cells were seeded only in the luminal space of the HFs (FIG. 7A). For co-culture, human lung microvascular endothelial cells (HLMVEC, Cell Applications) were seeded inside HF #2 and #4, and human bronchial epithelial cells (BEAS-2B, ATCC) were seeded inside HF #1, #3, and #5. To facilitate cell attachment, the HFs were coated with 30 μg/mL of fibronectin (BD Biosciences) and 50 μg/mL of collagen type I (rat tail, BD Biosciences), for the region growing HLMVE and BEAS-2B, respectively. The coated bioreactor was incubated at 37° C. for 1 hour and washed with PBS. The cell culture medium was injected into the device to replace the remaining PBS. The PBS was replaced with microvascular endothelial cell growth medium (Cell Applications) containing 100 U/mL of penicillin-streptomycin in HF #2 and #4 and the bronchial epithelial cell growth medium (Lonza) in HF #1, #3, and #5.

Image Analysis:

To observe the coverage and uniformity of seeded cells inside the HF, the HF was removed from the devices and cut longitudinally using surgical blades. The cells were then stained with NucBlue Live Cell Stain (Life Technologies) for 20 min. Distribution of the cells over the HF surface was observed and recorded using a fluorescent microscope. The cells were counted using ImageJ software (National Institutes of Health). Cell viability was verified using a LIVE/DEAD Viability/Cytotoxicity Kit (Life Technologies) to ensure the success of the seeding process and long term cell culture. Cut HFs were incubated in diluted calcein AM (2 μM) and EthD-1 (4 μM) solution and incubated at 37° C. for 30 minutes. The stained HFs were then observed using a fluorescent microscope (Z1 microscope, Zeiss). The shape of the cells and surface coverage on the HF was also observed with scanning electron microscopy (FEI, Inspect F SEM).

Results

Figure 5B:
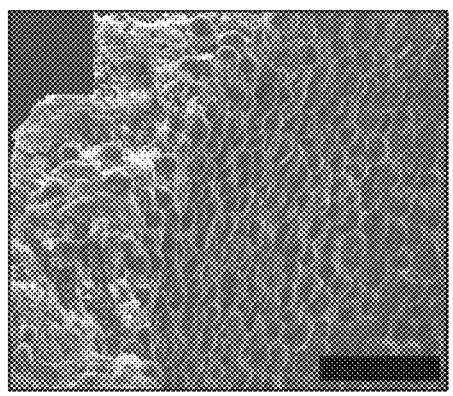
Figure 5C:
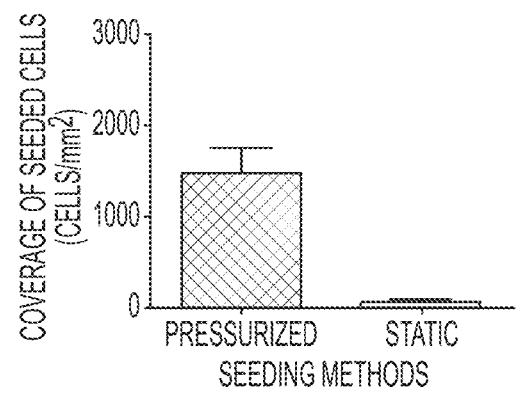
Figure 5D:
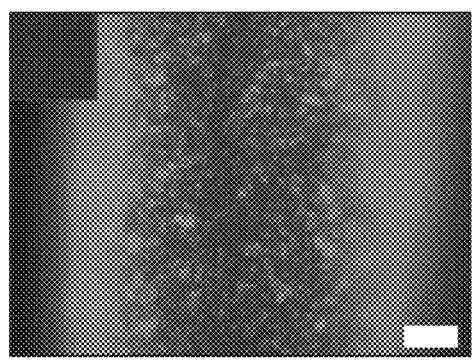
Figure 5E:
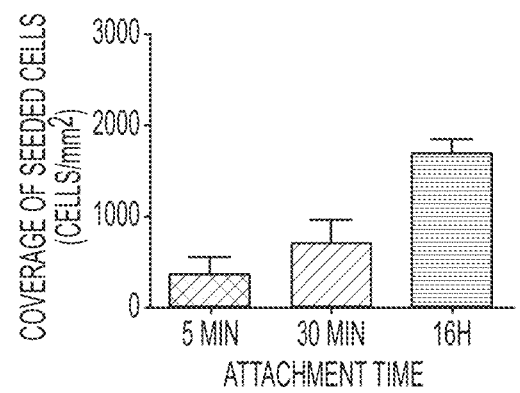

Cell seeding is an important step in any cell culture experiment involving adherent cells. The surface coverage of the seeded cells and their viability can fluctuate with variations in the seeding process. The static seeding process is the simplest and most widely used in adherent cell culture, where the technique relies on gravity and time to allow the cells to adhere to the surface. With 3D structures like the HF, application of static seeding may not ensure proper surface coverage throughout the entire luminal surface of a fiber. Since the HF has walls that are permeable to fluid, a dynamic cell seeding process was utilized to ensure higher surface coverage and reproducibility. By using a pressurized flow of the seeding solution through the luminal part of the HFs (FIG. 5A), it was possible to force the liquid pass through the membranes while leaving cells deposited onto the luminal surface. Using this technique it was possible to get cells deposited across the entire surface of the HF. FIG. 5B shows an SEM image of the inside of the HF after the cells were deposited into the luminal surface using the pressurized method. When the pressurized deposition method was compared to the static method, the pressurized method resulted in 22-fold more cell deposition on the HF walls (FIG. 5C). However, the pressurized process can impart stress on the cells during the deposition process, which may lead to cell death due to high shear. The ability of the cells to withstand the shear depends on the cell types. In this case, deposition using A549 cells by this method did not show significant cell death (quantified by the live/dead staining, FIG. 5D) after the deposition process. Nevertheless, the deposition did not lead to immediate cell adherence onto the surface. FIG. 5E shows the coverage of seeded cells that adheres to the surface over time. It took up to 16 hours for the cells to adhere to the surface.

Figure 6B:
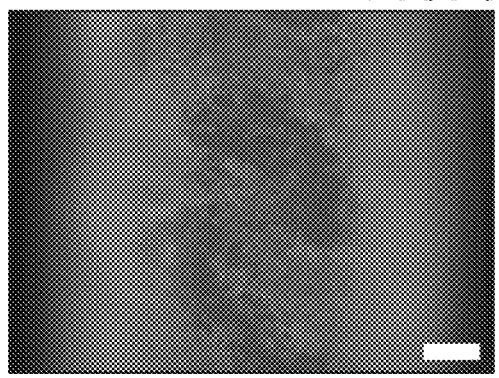
Figure 6C:
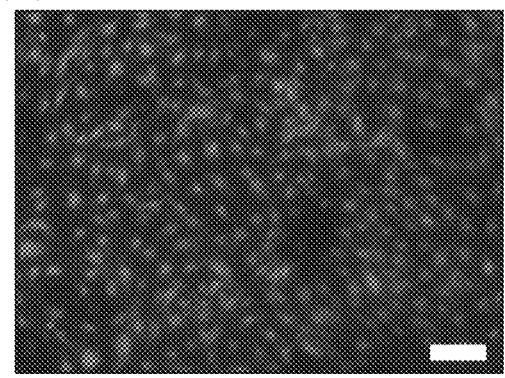

Different cells have different growth rates and may require different media for growth. Therefore, it is important for a platform to accommodate the ability to manage multiple fluids independently. The designs of the HF-integrated platforms were suitable to flow different fluids in the luminal and apical sides independently. For the single HF integrated system, it was possible to seed and grow BEAS-2B cells inside the HFs, while growing HLMVE cells at the bottom surface of the HF housing chamber (FIG. 6A). Both types of cells require different media for optimal growth. FIG. 6B and FIG. 6C show the live/dead staining of the two regions after five days of co-culture.

The co-culture approach in this configuration was similar to co-cultures carried out in commercially available Transwell plates (Miki et al., *J. Steroid Biochem. Mol. Biol.* 131:68-75, 2012), which have been used for tumor microenvironment applications. However, in this case, the HFs offer 3D scaffolds for the cells to grow. Unlike Transwells, which is a static culture system, the HF platform offers the ability to integrate flow and thereby enables long term cell culture. Additional flexibility of the integrated system is the ability to create flow conditions required by the overall co-culture process. In this case, a combination of flow-based (luminal side) and static (chamber side) cell seeding method was used, to seed the two types of cells. After the cells adhered to their respective surfaces, it was possible to switch to flow conditions (e.g., 10 μL/min on the luminal side and 10 μL/min on the chamber side).

Figure 7B:
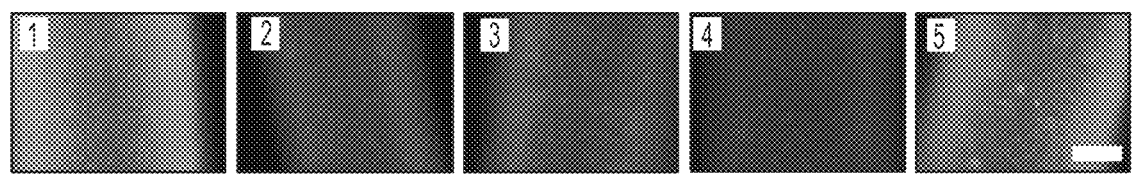

Similarly, on the multiple HF system, different types of cells could be cultured simultaneously inside the different HFs. FIG. 7A illustrates a co-culture experiment that was performed on a multi-HF integrated microfluidic system. Here, both cell types were seeded inside individual HFs using the dynamic seeding method. Since the cells were deposited on the luminal surface of the HFs, each HF can flow different media to aid the respective cell adherence and growth. After 5 days of culture, live/dead staining results showed both cell types maintained high viability (FIG. 7B). The ability to manipulate flow and the media type depending on the type of application with these HF integrated microfluidic platform can be used to generate diverse co-culture models for wide applications including drug development and regenerative medicine.

Example 3

Hollow Fiber Integrated Microfluidic Device with Pressure Modulation

FIG. 8 shows a schematic of an exemplary HF integrated microfluidic device that permits modeling of the effect of changes in pressure or extracellular matrix stiffness on cells. The device is shown in the context of modeling breast tissue (e.g., culturing multiple cell types present in breast tissue); however, one of ordinary skill in the art will recognize that the disclosed devices can be utilized with other cell types.

Figure 9:
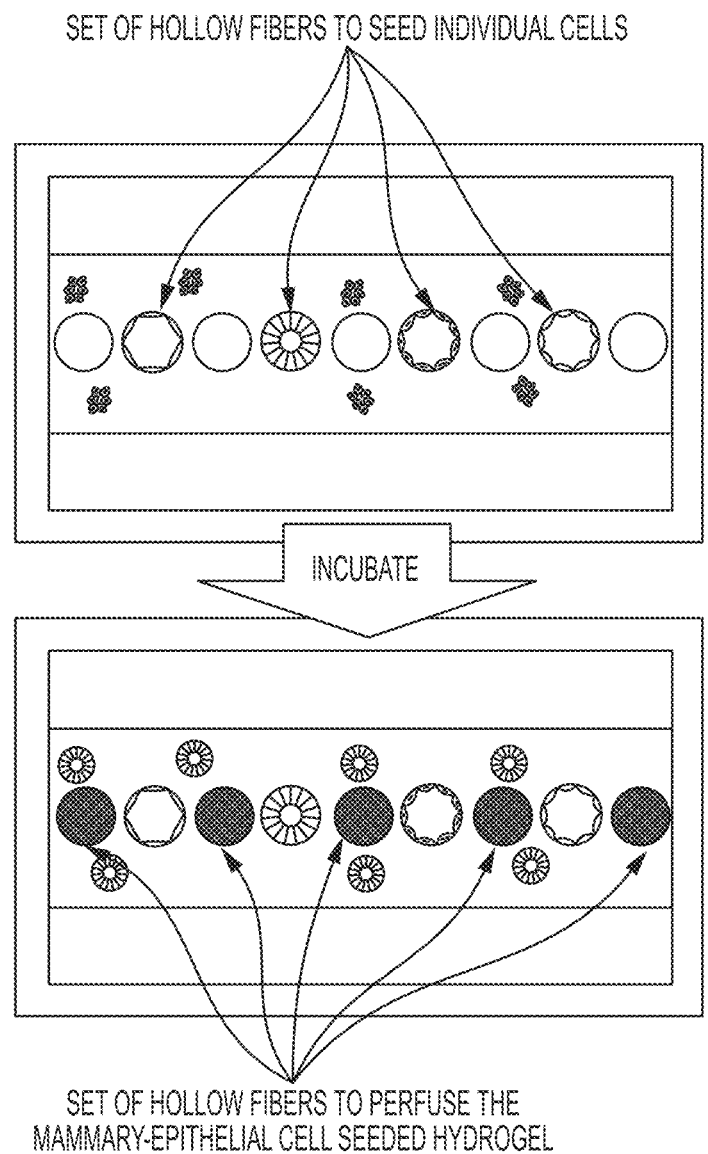
FIG. 9 is a schematic diagram showing a cross-section of the device shown in FIG. 8, during seeding of the first set of HFs and matrix with individual cells (top) and perfusion of the matrix (hydrogel) seeded with cells using the second set of HFs (bottom).

The device has three stacked chambers (inset of FIG. 8). The middle chamber houses one or more hollow fibers. In this embodiment, the middle chamber is filled with a hydrogel matrix (e.g., Matrigel® matrix). In some embodiments, multiple hollow fibers are integrated in the middle chamber. Two sets of hollow fibers are included. The first set of hollow fibers allows tissue culture with different types of cells. Each hollow fiber can be seeded with a cell of choice (which may be the same as or different from those in other HFs) and each cell type is cultured in their native media. Cell to cell communication is maintained through the pores of the hollow fiber and a common media is placed to fill up the space between HFs in the middle chamber (e.g., 1:1 collagen (Type 1) infused Matrigel). The gel matrix may also be seeded with cells (e.g., mammary epithelial cells in the embodiment shown in FIGS. 8 and 9). This gel is perfused with the appropriate media using a second set of hollow fibers that do not contain cells (FIGS. 8 and 9).

The bioreactor has ports from the side of the middle chambers to inject the hydrogel matrix (and cells, if desired). Filling up of the middle chamber with the hydrogel matrix is optimized such that minimal void space is created and the hollow fibers are not compressed during the filling process. Cell seeding inside the hollow fibers is carried out by injecting the individual cell types into individual hollow fibers (e.g., as described in Example 2). Each of these hollow fibers has isolated inlets and outlets to allow perfusion of the optimal media for the cell type in the particular HF.

The upper and lower walls of the middle chamber are fabricated using a flexible material (e.g., silicone) such that the hydrogel matrix can be compressed to change its stiffness. The upper and the lower chamber are filled with air, which is used to create a given pressure on the membranes (FIG. 10) and hold them to maintain a certain stiffness of the matrix. The middle chamber is connected to integrated vent channels, such that water from the hydrogel is passed into the vent channels after a given compression is applied. The reduction of water and the compression on the gel results in higher stiffness.

FIG. 11 shows a flow diagram and design of an exemplary integrated system for flow management for a HF microfluidic platform. The platform illustrates the management of at least five media (M1-M5) to be circulated into the bioreactor. The system integrates previously developed miniaturized peristaltic pumps, planar flow management systems, valves, and custom reservoirs (for example, those disclosed in WO 2016/049363 and WO 2016/049365, incorporated herein by reference), to enable long term tissue culture inside commercially available incubators. The hydrogel chamber is perfused with oxygenated media via multiple hollow fibers (FIGS. 8 and 9). This arrangement should create an oxygen gradient across the hydrogel and such gradient can be controlled by controlling the oxygenation of the media. The reservoir can have a wall made with semipermeable membranes to allow for gas exchange. Therefore, by controlling the concentration of oxygen inside the incubator, the oxygen gradients created inside the hydrogel chamber are controlled.

Example 4

Breast Tissue Model Microfluidic Device

The HF microfluidic device described in Example 3 is utilized to model normal breast tissue or breast cancer physiology. There the device includes a set of hollow fibers (for example, at least four hollow fibers) seeded with different types of cells (adipocytes, fibroblasts, microvascular, and myoepithelial cells) in individual hollow fibers. The middle chamber is filled with 1:1 collagen (Type 1) infused Matrigel and seeded with mammary epithelial cells such that they can differentiate into ductal and alveolar structures (e.g., Krause et al., *Tissue Eng. Par C: Meth.* 14:261-271, 2008). The gel is perfused with the appropriate media (Table 1) using a set of hollow fibers in the middle chamber that do not contain cells. The different cell types and media are provided in Table 1.

TABLE 1

Exemplary cells and media for breast tissue model

| Cell type | Cell Line | Medium | Cell/Medium Source |
|---|---|---|---|
| Adipocytes | Human Adipocytes | Adipocyte Differentiation Medium | Cell Apps. |
| Fibroblasts | MF-F | MF-1 | ZenBio |
| Microvascular cells | HUVEC | Endothelial Cell Growth Kit | ATCC |
| Myoepithelial cells | MBE-F | MEG-1 | ZenBio |
| Normal mammary epithelial cells | MLE-F | LCM-1 | ZenBio |
| Tumor mammary epithelial cells | MLE-F-TM | LCM-1 | ZenBio |

Cell seeding into the Matrigel matrix is carried out by methods described in Krause et al. (*Tissue Eng. Par C: Meth.* 14:261-271, 2008). The bioreactor has ports from the side of the middle chambers to inject the mammary epithelial cell-infused matrix. Commercially available hollow fibers (e.g., mixed cellulose ester HF with pore size 0.2 µm; lumen size 0.6 mm, Spectrum Labs, Rancho Dominguez, Calif.) that are sufficiently robust for handing/installation and can resist the compression force created during the hydrogel filling are utilized. Cell seeding inside the hollow fibers is carried out by injecting the individual cell types into individual hollow fibers. Each of these hollow fibers has isolated inlets and outlets to allow perfusion of the optimal media for the selected cell types. During the seeding process, the outlet of the hollow fibers is closed such that the media is forced to pass through the pores of the hollow fibers, leaving the cells seeded onto the luminal wall. The concentration of the cells in the seeding solution is optimized to obtain maximum coverage of the luminal wall during seeding.

After seeding, the outlets are opened to allow for perfusion using peristaltic pumps. The second set of the hollow fibers that were not seeded with any cells are perfused with media suitable for the growth and organization of the Mammary-epithelial cells. Individual hollow fibers in the first set with seeded cells are perfused with their optimal growth medium, respectively.

The cells utilized in these devices may have different growth rates and may need different lengths of time to become confluent (or to form ductal and alveolar structures in the case of mammary-epithelial cells). For example, acinar differentiation happens in 10 days, whereas mature adipocytes are expected 14 days after induction of differentiation. Therefore, a cell culturing strategy is used to introduce each type of cells at the appropriate time point.

The formation of tight junctions inside each hollow fiber is used as an indication of tissue formation. To evaluate the ability to form tissue, cells are observed at different time points after they are seeded inside the hollow fiber. Hollow fibers are not generally transparent. Therefore, hollow fibers are sacrificed at different time points and they are cut open, along the axis of the hollow fibers. Histological stains/microscopy are used to observe for cell viability (e.g., LIVE/DEAD Viability/Cytotoxicity Kit, Life Technologies) and tight junctions (e.g., ZO-1, Cell Signaling Technology). Initial experiments are performed on hollow fibers that are not integrated into devices for quick evaluation.

To examine the formation of ductal and alveolar structures by the mammary-epithelial cells, histological staining and confocal microscopy are used to obtain images at different depths (z). Z-stacking image reconstruction is employed to obtain an analysis of the mammary structures formation. Two models are developed—one with normal mammary epithelial cells and one with a mixture of normal and tumor mammary epithelial cells to represent both normal and cancer model of the breast tissue.

Long term culture (e.g., 21 days), is utilized to demonstrate the ability to perturb individual parameters to assess their distinct contributions. Systems with normal mammary epithelial cells are used as the control and to establish a baseline metabolite profile. Metabolite profiles are first investigated using two commercially available panel based clinical chemistry analysis tools namely, iSTAT (Abbott Laboratories) and the Piccolo (Abbott Laboratories). Liquid chromatography-mass spectrometry (LC-MS) based metabolic profiling is also used to establish a baseline of the key affected metabolites from the model. Since all the hollow fibers have individual flow paths, it is possible to collect isolated samples representing the metabolic changes occurring within each individual cell types due to the response of a perturbation. In some examples, stiffness of the ECM is dynamically changed to observe the impact on the mammary epithelial cells and all the other stromal cells in terms of metabolic activities. In other examples, metabolic changes due to changing oxygen gradients within the gel matrix are assessed.

Example 5

Analysis of Cell-Cell Communication with Tissue Model Microfluidic Device

A tissue model microfluidic device, such as those described in Examples 2-4 and FIGS. 8-13 is utilized to study cell-cell communication. Initially, two cell types at a time are co-cultured and then the number of cell types in the co-culture model is increased. The bioreactor device is designed to provide the unique ability to control (eliminate or introduce) the number of variables in the biological model arising from individual types of cells. In some examples, the cells include combinations of one or more types of stromal cells (e.g., microvascular cells, myoepithelial cells, adipocytes, and/or fibroblast cells) and mammary epithelial cells. For example, the combination of stromal cells with mammary epithelial cells is incrementally changed to collect the exosomes in the chamber and assign the respective exosome contents to that particular combination. By increasing the complexity in each experiments data to analyze the influence of stromal cells on characteristics such as epithelial-mesenchymal transition (EMT) and/or development of drug resistance are obtained.

Following a period of incubation, devices are sacrificed to collect the media from the chamber. Exosomes are collected from each set of experiments using commercially available kits. Collected exosomes are characterized for peptide and miRNA biomarkers. In addition to validation, experiments with normal mammary epithelial cells serve as the control. Identification of systems undergoing EMT is determined by tracking markers such as E-cadherin, EPCAM, and vimentin in the mammary epithelial cells. Markers for breast cancer cells that are drug resistant include STAT1, MX1, and OAS1. The peptide contents and RNA markers from control and cancer models are compared to identify biomarkers that change (for example, increase or decrease) during EMT. Statistical analysis of data from different experiments that use different combination of stromal cells is used to identify the role the stromal cells in exosome-mediated cell communication in EMT and metastasis or development of drug resistance.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A microfluidic device comprising:
   a first chamber filled with a hydrogel matrix and comprising two or more channels extending therethrough, wherein the two or more channels each comprise a central lumen, an elongated body with an inner surface and an outer surface, and an isolated inlet and outlet, wherein the first chamber comprises an upper wall, a lower wall, and at least two side walls;
   an inlet and an outlet fluidly coupled to the first chamber; and
   at least two openings in each of two opposite walls of the first chamber to accommodate the isolated inlet and outlet of each of the two or more channels, or tubing connected to the isolated inlet and outlet of each of the two or more channels,
   wherein at least one of the channels comprises a first population of cells associated with the inner surface of the channel and the first chamber comprises a second population of cells in the hydrogel matrix;
   a second chamber above and in contact with the upper wall of the first chamber; and
   a third chamber oriented below and in contact with the lower wall of the first chamber,
   wherein each of the upper wall of the first chamber and the lower wall of the first chamber comprise a flexible substrate;
      a fluid circuit board fluidly coupled to the isolated inlet and outlet of each of the two or more channels;
      one or more pumps fluidly coupled to the fluid circuit board; and
      one or more reservoirs fluidly coupled to the one or more pumps.

2. The microfluidic device of claim 1, wherein the hydrogel matrix comprises an extracellular matrix comprising one or more of collagen, laminin, fibronectin, heparan sulfate proteoglycans, entactin/nidogen, or elastin.

3. The microfluidic device of claim 1, wherein the two or more channels comprise one or more hollow fibers.

4. The microfluidic device of claim 1, wherein the flexible substrates are silicone.

5. The microfluidic device of claim 1, wherein the first population of cells and/or the second population of cells are cancer cells.

6. The microfluidic device of claim 1, wherein the first population of cells and/or the second population of cells are breast cancer cells or prostate cancer cells.

7. The microfluidic device of claim 1, wherein at least one channel does not comprise cells.

8. A method of culturing cells comprising culturing cells in the microfluidic device of claim 1, comprising:
   contacting the first population of cells with a culture medium; and
   incubating the cells under conditions sufficient for growth, survival, and/or differentiation of the cells.

9. The method of claim 8, wherein contacting the first population of cells with the culture medium comprises flowing the culture medium through the at least one channel comprising the first population of cells.

10. The method of claim 8, further comprising:
    contacting the second population of cells with a culture medium; and
    incubating the cells under conditions sufficient for growth, survival, and/or differentiation of the cells, wherein at least one of the channels does not contain cells.

11. The method of claim 10, wherein contacting the second population of cells in the first chamber with the culture medium comprises flowing the culture medium through the at least one channel that does not contain cells.

12. The method of claim 8, further comprising modulating pressure applied to one or both of the flexible substrates.

13. The method of claim 8, further comprising measuring one or more characteristics of the cells.

14. The method of claim 10, wherein the cells in at least one of the channels and the cells in the first chamber are different cell types.

15. The method of claim 11, wherein the culture medium is an oxygenated culture medium.

16. The method of claim 12, wherein modulating the pressure applied to the flexible substrates modulates the stiffness of the hydrogel matrix.

* * * * *